(12) United States Patent
Barash et al.

(10) Patent No.: US 10,178,534 B2
(45) Date of Patent: *Jan. 8, 2019

(54) COMMUNITY-BASED RESPONSE SYSTEM

(71) Applicant: ZOLL Medical Corporation, Chelmsford, MA (US)

(72) Inventors: David Barash, Boston, MA (US); Mark Totman, Silver Lake, NH (US); Gary A. Freeman, Waltham, MA (US); Timothy Sean McGough, Merrimack, NH (US)

(73) Assignee: ZOLL Medical Corporation, Chelmsford, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/927,851

(22) Filed: Oct. 30, 2015

(65) Prior Publication Data

US 2016/0100302 A1 Apr. 7, 2016

Related U.S. Application Data

(63) Continuation of application No. 12/946,803, filed on Nov. 15, 2010, now Pat. No. 9,232,040.

(Continued)

(51) Int. Cl.
  *H04M 11/04* (2006.01)
  *H04W 4/90* (2018.01)
  (Continued)

(52) U.S. Cl.
  CPC .......... *H04W 4/90* (2018.02); *G08B 21/0211* (2013.01); *G08B 25/005* (2013.01);
  (Continued)

(58) Field of Classification Search
  CPC ..... H04W 76/007; H04W 4/22; H04W 64/00; H04W 4/02; H04W 48/04; H04W 4/14;
  (Continued)

(56) References Cited

U.S. PATENT DOCUMENTS 5,166,972 A  11/1992  Smith
5,960,337 A   9/1999  Brewster et al.
(Continued)

FOREIGN PATENT DOCUMENTS

EP   1879370     1/2008
JP   08-005394   1/1996
(Continued)

OTHER PUBLICATIONS

Extended European Search Report, EP Application No. 10830876.8, dated Jun. 6, 2016, 7 pages.

(Continued)

*Primary Examiner* — Stephen M D Agosta
(74) *Attorney, Agent, or Firm* — ZOLL Medical Corporation

(57) ABSTRACT

A computer-implemented method for communicating information to medical responders includes registering a plurality of individuals as potential responders for medical problems, receiving at a central service an indication that a person is having a medical problem and receiving information that identifies a current location of the person, and identifying, from among the registered plurality of individuals, one or more registered individuals who are currently in close proximity to the person having a medical problem. The method also includes transmitting, to the one or more registered individuals, information that identifies the location of the person having a medical problem. The one or more individuals comprise lay responders who are not assigned responsibility to provide lifesaving services in an area around the current location of the person.

36 Claims, 15 Drawing Sheets

Related U.S. Application Data

(60) Provisional application No. 61/261,276, filed on Nov. 13, 2009.

(51) Int. Cl.

| | | |
|---|---|---|
| *G08B 21/02* | (2006.01) | |
| *G08B 25/00* | (2006.01) | |
| *H04M 1/725* | (2006.01) | |
| *H04W 4/02* | (2018.01) | |
| *H04W 4/12* | (2009.01) | |
| *G08B 25/01* | (2006.01) | |
| *G08B 25/14* | (2006.01) | |
| *G08B 27/00* | (2006.01) | |
| *G16H 40/20* | (2018.01) | |

(52) U.S. Cl.
CPC .......... *G08B 25/016* (2013.01); *G08B 25/14* (2013.01); *G08B 27/001* (2013.01); *G16H 40/20* (2018.01); *H04M 1/72536* (2013.01); *H04W 4/023* (2013.01); *H04W 4/12* (2013.01); *G08B 27/003* (2013.01)

(58) Field of Classification Search
CPC ............. H04W 84/12; H04L 29/08108; H04L 2012/5607
USPC ......... 455/404.1, 404.2, 414.1, 456.1–456.6, 455/457, 466; 370/310.2, 338
See application file for complete search history.

(56) References Cited

U.S. PATENT DOCUMENTS

| | | | |
|---|---|---|---|
| 6,492,581 B1 | 12/2002 | Russell | |
| 6,539,219 B1 | 3/2003 | Gallant et al. | |
| 6,694,299 B1* | 2/2004 | Barrer | G06Q 10/06 |
| | | | 705/2 |
| 6,747,556 B2 | 6/2004 | Medema et al. | |
| 6,920,204 B1 | 7/2005 | Tuttle | |
| 7,091,852 B2 | 8/2006 | Mason et al. | |
| 7,177,623 B2 | 2/2007 | Baldwin | |
| 7,379,015 B2 | 5/2008 | Workman | |
| 7,548,158 B2 | 6/2009 | Titus et al. | |
| 7,605,696 B2 | 10/2009 | Quatro et al. | |
| 7,609,819 B1 | 10/2009 | Tuttle | |
| 7,633,387 B2 | 12/2009 | Carmichael et al. | |
| 8,385,526 B2 | 2/2013 | Smelyansky et al. | |
| 2006/0084043 A1 | 4/2006 | Weaver et al. | |
| 2007/0108274 A1 | 5/2007 | Boardman et al. | |
| 2008/0098068 A1 | 4/2008 | Ebata | |
| 2008/0138778 A1 | 6/2008 | Eggert et al. | |
| 2008/0267360 A1 | 10/2008 | Spector | |
| 2009/0035740 A1 | 2/2009 | Reed | |
| 2009/0222539 A1 | 9/2009 | Lewis et al. | |
| 2009/0284348 A1 | 11/2009 | Pfeffer | |
| 2010/0250643 A1 | 9/2010 | Savage et al. | |

FOREIGN PATENT DOCUMENTS

| | | |
|---|---|---|
| JP | 2002-183380 | 6/2002 |
| JP | 2002-230672 | 8/2002 |
| JP | 2002-314715 | 10/2002 |
| JP | 2003-040061 | 2/2003 |
| JP | 2003-121162 | 4/2003 |
| JP | 2006-221109 | 8/2006 |
| JP | 2007-241502 | 9/2007 |
| JP | 7-334834 | 12/2007 |
| JP | 09-157485 | 7/2009 |
| JP | 09-224967 | 10/2009 |
| WO | 2004/057901 | 7/2004 |
| WO | WO2009/136259 | 11/2009 |

OTHER PUBLICATIONS

Chinese Office Action, CN Application No. 201080061194.6, dated Mar. 30, 2015, 17 pages.
International Search Report & Written Opinion for Application No. PCT/US2010/056755, dated Jan. 20, 2011, 13 pages.
International Preliminary Report on Patentability for Application No. PCT/US2010/056755, dated May 24, 2012, 9 pages.
Japanese Office Action, JP Application No. 2012-539062, dated Oct. 7, 2014, 5 pages.
Japanese Office Action, JP Application No. 2012-539062, dated Sep. 8, 2015, 10 pages.
Non-Final Reasons for Rejection, JP Pat. App. No. 2016-001800, dated Jan. 20, 2017, 7 pages.
Extended European Search Reprot, EP App. No. 10830876.8, dated Feb. 1, 2017, 12 pages.

* cited by examiner

COMMUNITY-BASED RESPONSE SYSTEM

CROSS-REFERENCE TO RELATED APPLICATIONS

This application is a continuation application and claims priority under 35 U.S.C. § 120 to U.S. patent application Ser. No. 12/946,803, filed on Nov. 15, 2010, which claims benefit under 35 U.S.C. § 119(e) to U.S. Provisional Application Ser. No. 61/261,276, filed on Nov. 13, 2009, the entire contents of which are hereby incorporated by reference.

TECHNICAL FIELD

This document relates to computer-based systems and techniques for providing response to emergency situations, such as traffic accidents, cardiac arrest, or other medical emergencies.

BACKGROUND

Sudden health problems such as sudden cardiac arrest and injuries caused by accidents kill thousands of people and cause permanent injury every year. Fast and competent care can be essential to positive outcomes in such situations. For example, it is said that the chance of surviving a sudden cardiac arrest falls by ten percent for every minute in delaying effective treatment.

Emergency events like sudden cardiac arrests and accidents are generally responded to by organized emergency response units, such as ambulance or fire crews, and by laypeople who are immediately around the events so that they personally witness or offer assistance for the events. Often, the laypeople in a victim's immediate vicinity are not trained to treat the victim, or are too overwhelmed to provide effective treatment. On the other hand, the organized emergency response units may be far away from the victim, so that they cannot arrive at the scene for a long time.

SUMMARY

This document describes systems and techniques that may be used to alert responders, including lay responders and professional responders, about an emergency situation. In this document, professional responders are the trained and organized responders who are assigned to cover, and are responsible for covering, a particular geographic area for rescue and emergency response, such as EMTs and firefighters who are assigned to an area. Lay responders are other responders who are available on an ad hoc basis in the area of an emergency event, but who are not agents of an organization that is responsible for providing emergency services in the geographic area. Lay responders may range from relatively untrained citizens, such as ordinary people who are CPR certified, up to highly-trained medical professionals who have indicated a willingness to be summoned to an emergency in their spare time and outside of any assigned geographic area that they may normally be assigned to as part of their job.

In the systems and techniques described here, citizens may register with a public on-line system to be lay responders. Such registration includes an agreement to have their location reported from their mobile computing device (e.g., smart phone/app phone) to the registration service. At a later time, an emergency call may come into a dispatch service, such as by a telephone call to a 911 operator. The dispatch service (e.g., through an employed human dispatcher) may enter the address for the call and may have a map of the area around the call brought up on a video monitor. The map may be populated with icons that represent the locations of registered responders, including lay responders whose locations are being reported (with their consent) by their portable electronic devices, in the geographic area around the call. The dispatcher may then choose to notify one or more of the lay responders, along with notifying a professional response crew. The map and associated database may also indicate the background or qualifications of the registered responders, so that a dispatcher may select a team of candidate responders, from all the potential lay responders in the area who are currently active, who have appropriate skill levels for the particular event.

Upon receiving a notification, each candidate lay responder may reply with an indication of whether they are willing and able to help with the call. If they indicate that they are willing to help, the system may automatically send to their mobile computing device a map that shows their current location, the location for the call (where the call is near the victim's location), a highlighted navigation route between their location and the location of the call, and possibly icons that indicate the locations of publicly-accessible equipment (first aid kits and automatic external defibrillators (AEDs)) that might be helpful in responding to the call and that the particular lay responder can grab on the way to the location of the call.

Using VoIP or other voice communication technologies, the system may also provide each of the responders, both lay and professional, with identification data for making voice connections with other of the responders, with the dispatcher, and with the original caller, which could be the victim or a person who first saw the victim and called in the emergency. Such a connection can be formed as a broadcast connection, so that every responder can hear any comment from any other responder, and the responders can thus coordinate their efforts as they close in on the area of the call. Also, certain of the persons may be able to control the types of connections, such as by a dispatcher choosing to speak directly to one of the lay responders privately and directly (e.g., to inform a highly trained physician about other lay responders who will be reporting to a scene).

Where a responder has on their mobile computing device sensors for gathering patient data, such as sensors for measuring heart rate, blood pressure, and the like, that information may also be passed back to the other responders and to the system as a whole. Moreover, an identifier, such as a hyperlink, may be provided to hospital personnel where the patient is likely to be taken, and personnel at the hospital make click on the link to be brought into the system and to see the action unfold in real-time, including seeing data from sensors that are measuring the condition of the patient, viewing real-time video from one of the responders, and simply listening to the discussions of the responders (and perhaps jumping in and providing guidance and instruction to the responders).

Finally, the system may be programmed to format the various types of information that were gathered during an emergency response into a report. Such information may include digital files of conversations between and among the responders, data indicating paths taken by responders in reaching the location of the call, data from sensors about the victim's status, and the like. The report may be used, for example, to perform a debriefing for the team of responders so as to determine what was done well and what could be done better. In addition, the report may be used to promote certain responders who respond frequently and perform well, so that they are indicated to dispatchers as being effective responders, and are thus more likely to be selected by dispatchers for future calls.

Such systems and techniques can, in certain implementations, provide one or more advantages. For example, by identifying lay responders in the vicinity of a victim or victims, the systems and techniques can reduce response time for an emergency, which can be critically important for cardiac arrest victims. Also, responders may be shown the location of known publicly-accessible equipment, so that they can get it on the way to tending to the victim. The lay first responders may also communicate with the professional responders and with hospital staff to receive instruction and guidance, and also to tell the professional responders precisely where the victim is located. In addition, the systems and techniques here may be used to assemble an appropriate response team. In particular, a human or automatic dispatcher may select potential responders who are shown to have complementary skills, and may also assign tasks to each responder before they arrive on a scene, such as by assigning a first responder to provide chest compressions as soon as possible (especially if that responder has been shown, through training exercises that employ the accelerometer on their mobile device, to be good at performing chest compressions), assigning a second responder to get a defibrillator and related supplies needed treat cardiac arrest, and assigning other responders as appropriate (e.g., to meet and guide the professional responders when they arrive). In addition, for a multiple-victim emergency, each responder may be assigned to tend to a particular victim and/or task. Where there is a mass casualty situation, responders may be formed into teams, so that the least trained responders are grouped with responders who have more training, and so that each team may be well balanced.

Also, to help preserve order, particularly in mass casualty systems, a particular responder may be assigned as a lead responder, at least until professional responders arrive on site. A central organizer of the responders may also be provided off-site. A dispatcher could perform such a role, or could hand off such responsibility to another person and go back to his or her dispatching duties. The new controller of the system could be, for example, a trained medical director who could be "patched in" to the case and would be able to provide verbal instructions to the rescuers by voice connection and could also receive important data from the site, such as vital signs of victims.

Dispatchers and medical directors may also be provided with an intuitive, graphical interface by which they can deploy responders and manage them as they respond to an emergency. Such systems and techniques may also allow information about the victim's status to be transferred automatically to hospital staff so that they can begin treating the victim immediately upon arrival at the hospital. Moreover, the various information relating to a response may be saved and organized automatically, so that lessons can be learned about how to improve the response efforts.

Such systems and techniques may also depend on CPR feedback mechanisms that are programmed into electronic devices used by the responders, such as into smart phones that the users separately own. Such devices may include accelerometers whose outputs may be measured and double integrated to determine a distance that a responder is moving a victim's chest, and a rate at which the chest compressions are repeated. The device may then indicate on a display or may state audibly messages such as "push faster" or "push slower," or "push harder" or "push softer." Such functionality may also be incorporated into devices that are adjunct to a computing or communication device used by a responder, such as in a jacket that a user may purchase to wrap around and protect their device. For example, a force sensor could be created by placing two metal plates in a smart phone skin, so that the plates act as a capacitor and the distance between the plates represents the amount of force that a rescuer is applying to a patient's chest if they are pressing the device and jacket under their hands when performing chest compressions. Where such a chest compression measuring device is provided separately from the user's communication device, the two devices may or may not communicate with each other. For example, the jacket or skin could communicate via a physical connection to a smart phone or similar communication device (e.g., a media player having communications capabilities), and the communication device may then transmit the information to a central system.

Where such a measurement device is used, a responder's proficiency with CPR can be measure using such a device. Determinations may then be made about the responder's capabilities, and the responder may be given a skill ranking from practices exercises that the responder may perform using the device, so that the responder may be dispatched more readily or less often, or to assign each responder a role that matches the responder's skill set.

In one implementation, a computer-implemented method for communicating information to medical responders is disclosed. The method comprises registering a plurality of individuals as potential responders for medical problems, receiving at a central service an indication that a person is having a medical problem and receiving information that identifies a current location of the person, and identifying, from among the registered plurality of individuals, one or more registered individuals who are currently in close proximity to the person having a medical problem. The method also comprises transmitting, to the one or more registered individuals, information that identifies the location of the person having a medical problem. The one or more individuals comprise lay responders who are not assigned responsibility to provide lifesaving services in an area around the current location of the person. Registering the plurality of potential responders can comprise posting a sign-up software application that is internet accessible, and registering volunteers from the public using the sign-up application. The method can also include verifying with a third-party organization that the volunteers are qualified to provide a predetermined level of medical care. The method can also include verifying that the volunteers are qualified to provide a predetermined level of medical care comprises verifying that the volunteers are CPR-certified. Moreover, the method can additional comprise periodically determining whether the volunteers are qualified to provide a predetermined level of medical care, and removing volunteers for consideration as responders for medical problems if they do are no longer qualified to provide the predetermined level of medical care.

In some aspects, transmitting information that identifies the location of the person having a medical problem comprises identifying a device identifier corresponding to the one or more registered individuals and transmitting the information to a device that corresponds to the device identifier. The method can also include transmitting to the one or more registered users information that identifies locations of registered medical equipment near the person having a medical problem. In addition, the method can include receiving a response from a first of the one or more registered users and automatically making a voice connection between a portable telephone corresponding to the first of the one or more registered users and another of the one or more registered users or a dispatcher. The method can also include transmitting to the one or more registered individuals an invitation to respond to the person having the medical problem, determining whether a first of the one or more registered individuals has responded affirmatively to the invitation, and transmitting information that identifies the location of the person having a medical problem to the first registered individual only if the first registered individual has responded affirmatively.

In one aspect, the method further comprises receiving from a device assigned to one of the one or more registered individuals, data gathered from the person having the medical problem by sensors on the device, and storing the received data in association with an event identifier that corresponds to activities surrounding the medical problem. The method can also include storing information received from the one or more individuals during activities surrounding the medical problem, and provided the stored information for analysis. In addition, the method can include adjusting a rating for at least one of the one or more registered individuals based on the stored information, wherein the rating indicates the individual's proficiency in responding to medical calls.

In yet other aspects, the method can additional comprise changing a procedure for dispatching responders to emergency calls by analyzing the stored data. Moreover, the method can include providing to devices corresponding to the one or more registered individuals, data for automatically generating a map showing a location of the person having a medical problem and a location of the one or more registered individuals.

In another implementation, a computer-implementation system for coordinating actions by responders to an emergency event is disclosed. The system includes a dispatch server arranged to receive notifications of emergency events from reporting callers and to provide for dispatch of professional responders, and a notification system to identify lay responders who are in a vicinity of reported emergency events and notify the lay responders about reported emergency events in their area, wherein the lay responders are not assigned responsibility by a lifesaving organization to serve emergency events in their area. The system also includes an inter-respondent communication system programmed to make automatic electronic voice connections between professional responders for an emergency event and lay responders who have identified themselves as available in response to a notification from the notification system. The system can also include a publicly-accessible application store that makes available an application for practicing CPR chest compressions and for registering volunteers from the public to be identified as lay responders by the notification system.

In some aspects, notification system is further programmed to verify with a third-party organization that the volunteers are qualified to provide a predetermined level of medical care. Also, verifying that the volunteers are qualified to provide a predetermined level of medical care can include verifying that the volunteers are CPR-certified. The notification system is further programmed to periodically determine whether the volunteers are qualified to provide a predetermined level of medical care, and to remove volunteers from consideration as responders for medical problems if they do are no longer qualified to provide the predetermined level of medical care. The notification system can include a responder tracker programmed to identify a location of the person having a medical problem, identify a device identifier corresponding to the one or more registered individuals, and transmit data representing the location to a device that corresponds to the device identifier.

In certain aspects, the notification system is further programmed to transmit to the one or more registered users information that identifies locations of registered medical equipment near the person having a medical problem. The system can also include a voice communication system for automatically making voice connections between communications devices that are registered in the notification system as belonging to the one or more registered lay responders. In addition, the notification system can be programmed to transmit to the one or more lay responders an invitation to respond to an emergency event, to determine whether a first of the one or more lay responders has responded affirmatively to the invitation, and to transmit information that identifies a location of the emergency event to the first lay responder only if the first lay responder has responded affirmatively.

In certain aspects, the system also includes an event database storing information received from lay responders during activities surrounding an emergency event, and organized to provide the stored information for analysis. The system also includes a rating module programmed to adjust ratings for lay responders based on the stored information, wherein the ratings indicate a lay responder's proficiency in responding to emergency events. Moreover, the system can include a mapping server to provide to devices corresponding to lay responders data for automatically generating a map that shows a location of the emergency event and a location of one or more lay responders.

The details of one or more embodiments are set forth in the accompanying drawings and the description below. Other features and advantages will be apparent from the description and drawings, and from the claims.

DETAILED DESCRIPTION

Figure 1:
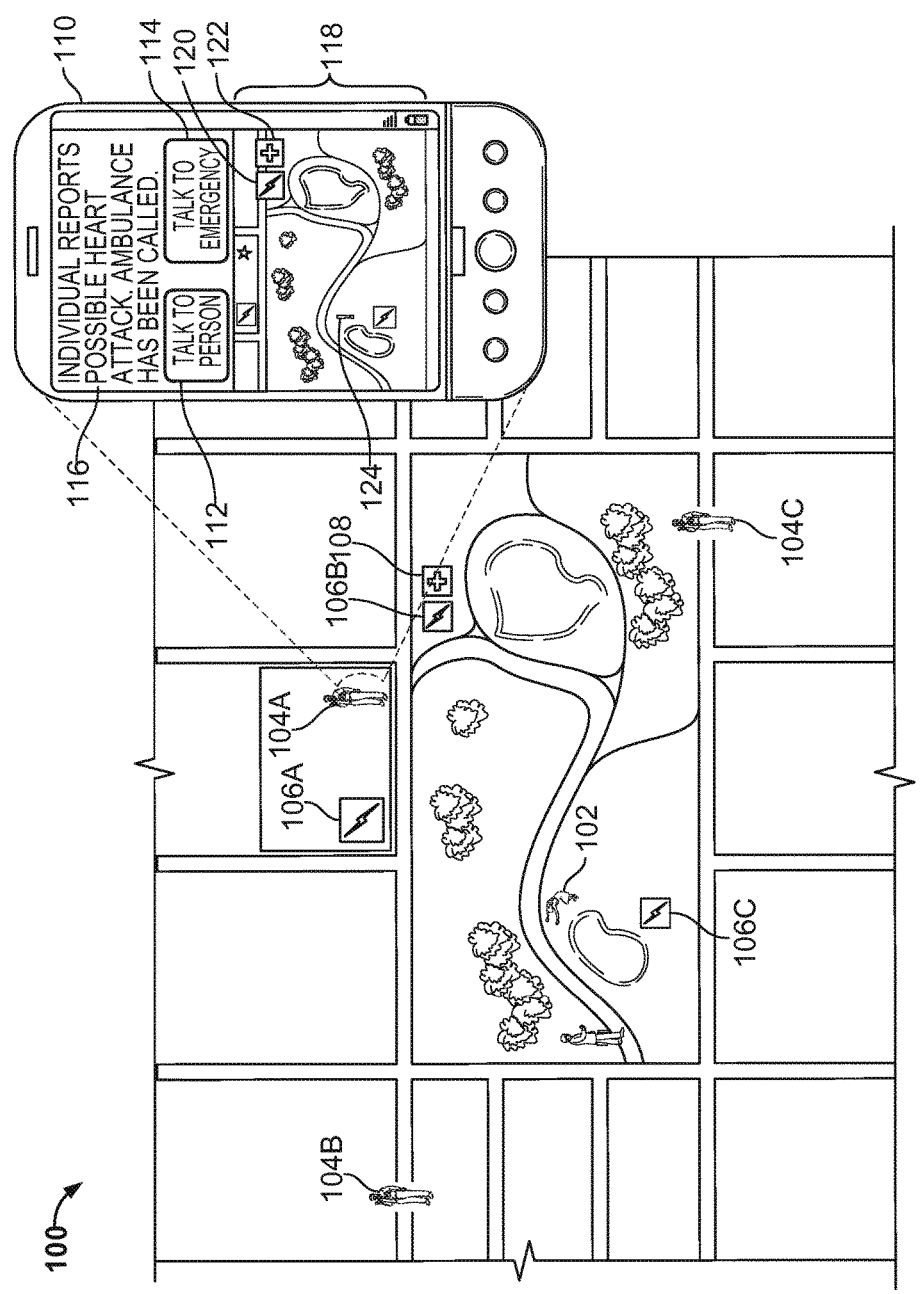
FIG. 1 is a conceptual diagram showing computer-guided emergency response by lay responders.

FIG. 1 is a conceptual diagram showing computer-guided emergency response by lay responders. In general, the figure shows a conceptualized version of a map for an area around a park in a metropolitan geographic area. An emergency event has recently occurred in the park, and various responders (designated by the letter "R") in the area of the event are shown converging on the location of the event (designated by the character "!"). The map is overlaid with icons that represent various objects in the area, including a victim 102, various responder's 104A-C, and pieces of emergency response equipment 106A-C and 108. The figure also shows a representation of a screen for a smart phone 110 to indicate an example graphical user interface (GUI) that may be shown to a lay responder 104A who has chosen to volunteer to respond to a call in the area. The discussion with respect to this figure is intended to indicate in general ways how responders may be organized and notified, and how they may communicate with each other, in order to improve response to an emergency condition, such as a call about a person suffering from sudden cardiac arrest, or a mass emergency having multiple victims for which responder coordination is important.

In the figure, the victim 102, indicated by an exclamation point (the location of the victim and the location from which a call reporting the event originated are presumed to be the same in the absence of addition information), has suffered a sudden cardiac arrest while running on a trail near a pond in the park. Upon feeling chest pains, the victim 102 may have called 911 in order to report an emergency, or may have activated an application installed on his or her smart phone, where the application is programmed to initiate a call to emergency services and to provide data that indicates the victim's 102 geographic location. The victim 102 may have installed the application (e.g., from a public app store) if he had previously suffered chest pains or other indication of heart disease. The application, when executed, may permit a user to select an on-screen icon and then respond to fairly simple queries to indicate a condition that they are suffering (e.g., "I am short of breath" and/or "I am feeling severe chest pains" and/or "I feel numbness").

The application may then be programmed to report the information to a central service, such as a service that controls 911 intake and dispatching. The application, in doing so, may also report the user's current location, as measured from global positioning system (GPS) sensors on the user's smart phone. A general location for the user may also or alternatively be obtained by the central service by using cell tower triangulation or similar services, such as the GOOGLE MY LOCATION service.

Alternatively, the call to the central service may be made by telephone, either by the victim 102, or by a citizen who has come upon the victim 102 and has recognized that the victim 102 is in trouble. The telephone call may be made to a 911 number in a familiar manner, and the caller may provide a 911 operator with their current location. In this example, the caller may have provided the name of the park and have indicated that they are near the small pond in the park. The 911 operator or dispatcher may then use various tools to create a more specific location identifier for the call, such as by typing in the name of the park to bring up a map, such as from GOOGLE MAPS, and then pressing on a touchscreen near the small pond on the map to assign a presumed location for the event. The dispatcher could also draw a circle around the area that corresponds to the area reported by the caller, to indicate their uncertainty of location with respect to the location of the caller (e.g., a circle all the way around the small pond in this example). Such uncertainty could also be shown, for example, when a caller indicates that they are at a particular intersection, and the dispatcher does not know on which corner of the intersection the caller is located, or when the caller indicates that they are between two cross streets on a particular street and the dispatcher does not know at what location along the block the caller is located. As described below, the level of uncertainty may then be displayed to responders on maps that they see, so that they know where they will need to search for the event. The dispatcher may then choose, at the dispatcher's discretion, to alert registered responders who are registered with the system and who may be in the area around the park. Such an alert may be sent in coordination with an alert to professional responders who are assigned to cover the area. The dispatcher may choose to alert lay responders in addition to professional responders when it appears that the professional responders will take substantially longer to respond to the emergency then will the lay responders. As discussed in more detail below, the dispatcher, upon pulling up the map around the area of the victim 102, may choose to see an overlay, or layer, on the map of all possible registered responders in the area. The lifesaving capabilities of each responder may also be shown so that the dispatcher can determine whether the responders have a low level of training, or are highly experienced medical personnel. From such an interface, the dispatcher can press on icons that represent certain potential responders to choose them as candidate responders, and may then make other selection to have notifications sent to each of those candidate responders regarding the emergency.

The notification may be made automatically in cooperation with client-side applications that the candidate responders have previously installed on their individual smart phones, or a message may be sent to each smart phone causing a predetermined display to be shown on each smart phone, and for the smart phone to make a particular notification sound or vibration so that the candidate responders will recognize it as a call for an emergency. For example, the smart phone 110 of candidate responder 104A may have been caused to make the sound of an ambulance siren so that the responder 104A can distinguish the alert from a normal incoming telephone call, and may be more likely to pick up their smart phone 110 and respond to the call.

Other communication devices may also be employed by the lay responders. For example, a lay responder may have only a basic cellular telephone, and they may be notified and may respond by way of text messaging. In such a situation, information about the location of the event may be in text, and the responder may reply to messages in a familiar manner. Also, a skin on such a basic telephone may supplement the telephone with functionality like that discussed here for more advanced communication devices, such as an accelerometer or force sensor. In such a device, the supplemental functionality may simply generate feedback to a user, but not be able to transmit data directly up to a central system.

The map in FIG. 1 also shows iconic representation of equipment that is in the geographic area of the victim 102, and that may be accessible to responders who agree to help with the emergency situation. For example, icons having thunderbolts on them represent AED's that a responder may grab and take to the victim 102 when the victim has suffered a sudden cardiac arrest. Icons having a "+" on them may represent first aid kits that responders could use to bandage or otherwise treat victims of an accident. As described more fully below, the existence and locations of the various pieces of equipment may initially be enrolled by owners of the equipment who want to make it available in emergency situations, and registered volunteers may periodically survey various areas to locate the equipment and to verify that it is still there, is operational, and is publicly accessible. Also, the equipment may include wireless functionality by which it reports itself in to a network, such as via a 3G interface, WiFi interface, WhisperNet-type interface and the like. An owner of such a device may then "open" the device to inspection by a lifesaving system, which may then periodically seek and receive reports on the current status of the device. In certain instances, such a system (which could be operated by a non-profit organization) may trade free monitoring of device status in exchange for the device owner agreeing to open the device for public use when it is needed.

The equipment may also be associated with a schedule during which it is available, so that the system may filter the display of equipment, so as not to show equipment that is not currently available. As one example, a coffee shop near the park may keep an AED near its counter where it cannot be stolen, but may be willing, as a gesture of good will, to have responders run into the shop and borrow the AED if it is needed in the area. Such an AED may be shown to responders on their devices if an emergency arises during the shop's hours of operation, but not shown after hours.

Referring now more specifically to the smart phone 110 of responder 104A, the screen of the smart phone 110 shows an example of what the responder 104A may see after she has been notified about the victim's 102 problem and has affirmatively responded that she would like to take part in the response—thus converting herself from a candidate responder to a confirmed responder.

Upon the user 104A making such an indication, the dispatcher and/or a related automated system may download to the smart phone 110 information to allow the responder 104A to locate the victim 102, to show any relevant equipment in the area on the way to the victim 102, and to communicate to other responders who may be en route to helping the victim 102. Such information may be provided to the responder in a variety of manners, and in this example has been provided in the form of a webpage mash-up document that includes custom text about the victim 102, selectable controls by which the responder 104A may interoperate with the system, and a map with a navigational route to guide the responder 104A to the victim.

Such information may be provided using known techniques, such as asynchronous JavaScript and XML (AJAX), so the responder 104A may interact with the information in a rich manner without requiring multiple downloads of web pages every time the responder asks for additional information or alters the display (e.g., by panning or zooming the map). Also, the information may be provided from multiple sources (e.g., the dispatch system, a voice communication system, a map server, live cam scene video, and the like), either directly to the smart phone 110 or through one of the other services.

Referring now to the particular information displayed on the smart phone 110, and starting from the top of the display on the smart phone 110, there is shown a textual report 116 regarding the problem with the victim. The report 116 indicates that the victim has reported a possible heart attack and an ambulance has been called. The text for this report 116 may have been typed in manually by a dispatcher and provided to the responder notification system, or may have been generated automatically, such as in response to the victim 102 (or a witness near the victim 102) indicating to an application on the victim's smart phone that they believe they were suffering chest pains and could be having a heart attack. In addition, voice from the victim or a bystander could be directly transmitted to the responder as a voice file or as a text file converted from voice, using a speech-to-text converter. A direct voice channel may also be opened between one or more of the responders and the victim 102, e.g., so that they can receive directions form the victim (or from the person who is with the victim 102), can obtain information about the victim's 102 condition (so that, for example, they can determine that they need to obtain additional responders or additional equipment on the way to the victim 102), and can offer guidance to the victim or the person who is with the victim.

Additional text may also be provided either initially when the responder 104A becomes a confirmed responder, or at a later time. For example, a dispatcher may type additional information that may be sent out to all responders, both lay and professional, regarding updated information on the victim. For example, the dispatcher may have learned that the victim is a diabetic or has other issues that the responders should be aware of. That information may be provided in the textual area of the report 116 so that the responders may immediately see it if they are looking at their devices while they run or otherwise make their way toward the victim 102. Earlier text may be scrolled upward as additional text is added to the report 116, and a "chat" box may also be shown so as to allow multiple-way communication among the dispatcher and the responders. The chat text may be populated directly by typing of various users, or by users speaking and their spoken words being converted into text. All such spoken communications between and among the people involved in the event may also be converted in a similar manner to be stored with a summary report for the event.

Below the report 116, are two selectable controls 112 and 114. Selectable control 112, when selected by the responder 104A, will create a voice connection between the responder 104A and the victim 102. Such a connection may be made in a variety of manners. For example, the initial information provided to the smart phone 110 may include a URL, IP address, or other information needed to make a voice over IP (VoIP) connection between smart phone 110 and a device used by victim 102 or a person who is attending to victim 102 and who called in the emergency. The connection may also be made by a VoIP connection from the device 110 back to a dispatch center, and then to a telephone used by the victim 102, by an ordinary telephony connection, particularly when the telephone used by the victim 102 (or by one of the responders) is not a smart phone or other sort of mobile computing device that can make a VoIP connection. This voice connection may be used so that the responder may be given a preview of the problem the victim 102 is facing, or to allow the person attending to the victim to guide the responder 104A to the proper location.

Selectable control 114, when selected, connects the responder 104A to whatever professional responders have been dispatched by the dispatch center. Alternatively, selectable control 114 may connect the responder to the dispatcher. Thus, the responder 104A may report his or her current location (though the location could also be reported automatically from GPS readings captured by the application on the responder's communication device) and the fact that, for example, he or she plans to stop and grab an AED 106A or 106B on the way to the event. The emergency personnel, or professional responders, may confirm such a plan of action or may direct the responder 104A to do other things via the voice communication channel. In addition, selectable control 114 may permit responder 104A to communicate with responders 104B and 104C if they have become confirmed responders. In this manner, responder 104A may indicate that he or she will bring an AED, so that the other responders (104B and 104C) do not go out of their way to gather the defibrillator at 106C. Such communication may be arranged to occur like radio communications, so that any responder can speak by holding selectable control 114, and all of the other responders who been confirmed by the dispatch center will hear what is being said by that person. In this manner, the various responders can coordinate their activities quickly while still moving quickly and with minimal distraction toward victim 102. As noted, the communication may also be point-to-point between particular of the parties, and additional controls may be provided to establish various predetermined communication links automatically.

The bottom of the display for smart phone 110 is taken up by a map 118 which may be generated from a combination of data sources using known techniques such as those for creating mash-ups with GOOGLE MAPS. For example, the dispatch center may provide a latitude and longitude for responder 104A and a latitude and longitude for victim 102, to a navigation system that is publicly available (via a published application programming interface (API)), and a navigation system may respond by providing data for drawing the map overlaid with a thick navigation route line for an optimal path between the two points for the responder 104A. This path may be superimposed on the map 118 that responder 104A is shown. Other paths may be similarly superimposed over maps shown to responders 104B and 104C. In addition, actual icons 120 and 122 are superimposed on the map to show the responder 104A where relevant equipment is located near their route between their current location and the victim 102. The gathering of the information that is overlaid on the map may be by a server system before sending such information to the various client devices, or the server system may send information to the client devices, which may in turn automatically contact third-party mapping and navigation services (e.g., using their on-board applications and/or JavaScript provided to them by the server system) to generate the displays shown here.

The responder 104A may interact with the map 118 in familiar manners, including panning and zooming so as to see more detail or to see more of the surrounding area. For example, as shown in the figure, responder 104A is zoomed in too far to see responders 104B and 104C. As a result, responder 104A may want to zoom out so as to see more of the area and to obtain a better overview of what is occurring around the victim 102. The particular zoom level that is initially presented to the responder 104A may be selected automatically by the system so that both the location of the responder 104A and of the victim 102, as represented by icon 124 on the map 118, are shown on the smart phone 110.

As noted, each of the responders, both lay and professional, may be provided with a similar presentation to that shown on smart phone 110, though the star icon would represent their location, and other information would be personalized to them in an appropriate manner. Also, the professional responders may be provided with a display or with controls that differ significantly from those for the lay responders. For example, the professional responders may be provided with the ability to speak to each of the lay responders individually (e.g., if one of the lay responders is identified as a particularly experienced physician who the professional responders can depend on to lead the other responders), and the professional responders can be allowed to listen to any communications made by any of the lay responders, even if the other lay responders cannot hear them.

Also, though the lay responder's device 110 is shown and described as a smart phone in this example, it may take a variety of other forms. For example, the device could be a cellular telephone having text messaging capabilities, so that the user can receive direction via text message. The device could also be a portable networked device that does not have direct telephony capabilities such as an IPOD TOUCH media player or similar device. Other devices such as tablet PC's and other portable communication devices may also be used. In addition, certain of the functionality described above and below can be provided as part of an accessory to the relevant electronic communication, such as by placing a force sensor, temperature sensor, accelerometer, pulse sensor, blood pressure sensor, or other sensor in a plug-in module and/or jacket that a user can purchase for their electronic communication device (though such sensors may also be integrated into the device where appropriate).

In addition, other normal components of a smart phone or other communication device could be used as relevant sensors. For example, a pressure sensitive touch screen could be used as a force sensor by accessing, through the device's operating system, signals coming from the screen. Where the screen is a capacitive or impedance-based touch screen, the sensed signals could also be used for pulse measurements. For example, the field lines from such a screen extend outward from the front of the screen, and the screen could be pressed against the side of a victim's (or other person's) neck to measure changes caused by the periodic rush of blood through the victim's carotid artery. Touch screen sensors are also two-dimensional sensors, so that the exact positioning of the device would not be critical, and irregularities in positioning could be adjusted for by the software on the device. Such measurements could then be reported back to a central system automatically, such as to communicate the victim's vital signs to professional responders or to remote medical professionals who can advise the lay responders, including physicians at a hospital where the victim is likely to be transported.

The central system may be integrated into the on-site rescue work in various other manners as well. For example, local hospitals may be made part of a communication session so that on-site rescuers can identify the number of victims that the hospitals are likely to receive, and the approximate time until the victims will arrive. In such a situation, members of the overall communication session may choose to filter communications into sub-groups so that they see or hear only messages that are relevant to them, using techniques such as subscriptions to "channels" having messages that are tagged with items such as "hash tags" that are used to filter communications on social networks such as TWITTER.

In addition, the central system may be used to provide electronic medical record (EMR) data about particular victims to rescuers in the field. For example, a victim may be identified and a physician at a central hospital may cause certain information about the victim to be provided to rescuers, consistent with applicable privacy regulations. As one example, the physician may identify the victim's blood type to rescuers, or identify any potentially dangerous allergies or drug interactions. Such information may also be automatically filtered from an EMR and delivered to the rescuers.

In certain situations, the victim's smartphone may be used to provide EMR-related information about the victim to rescuers. For example, users of smartphones may input information to their phones about their blood type, allergies, medications, and other relevant information (e.g., if they have hepatitis or diabetes). Such information may then act as a form of electronic med-alert bracelet. Their device may also filter the data, such as by showing limited information (e.g., blood type and a person to contact when there is an emergency) on a home screen when the device is locked (where devices currently show the time and may permit dialing of 911 and other emergency numbers), and show all the information when unlocked (in addition, the phone when unlocked can access EMR-related information for the victim from a remote server system). The information may be indicated on the home screen by a red cross or other icon, and selection of the icon by a rescuer may cause a page of relevant information to be displayed. In addition, a patient's medical information may be stored on an amulet or other article that the victim may wear (such as by using RFD technology), and the information may be read by a standard smartphone of a rescuer, such as by using known near-field communication techniques. The information, when stored electronically in any of these ways, can be transferred automatically to an electronic device of a rescuer, such as a tablet computer for an EMT, and may be saved, transferred (e.g., to a target hospital), and used in various appropriate manners in the treatment of the victim.

In addition, a victim may provide basic medical record information to a publicly-accessible service, and the information may be indexed in an appropriate manner so that it can be retrieved on-site by a rescuer, as one example, the victim may be provided with a med-alert label for his or her smartphone, and may write an index number on the label that a rescuer can submit to the service in order to get the victim's information. Such an index number may also be the telephone number of the victim's mobile telephone, and that number may be displayed on a locked home screen of the telephone.

Figure 2A:
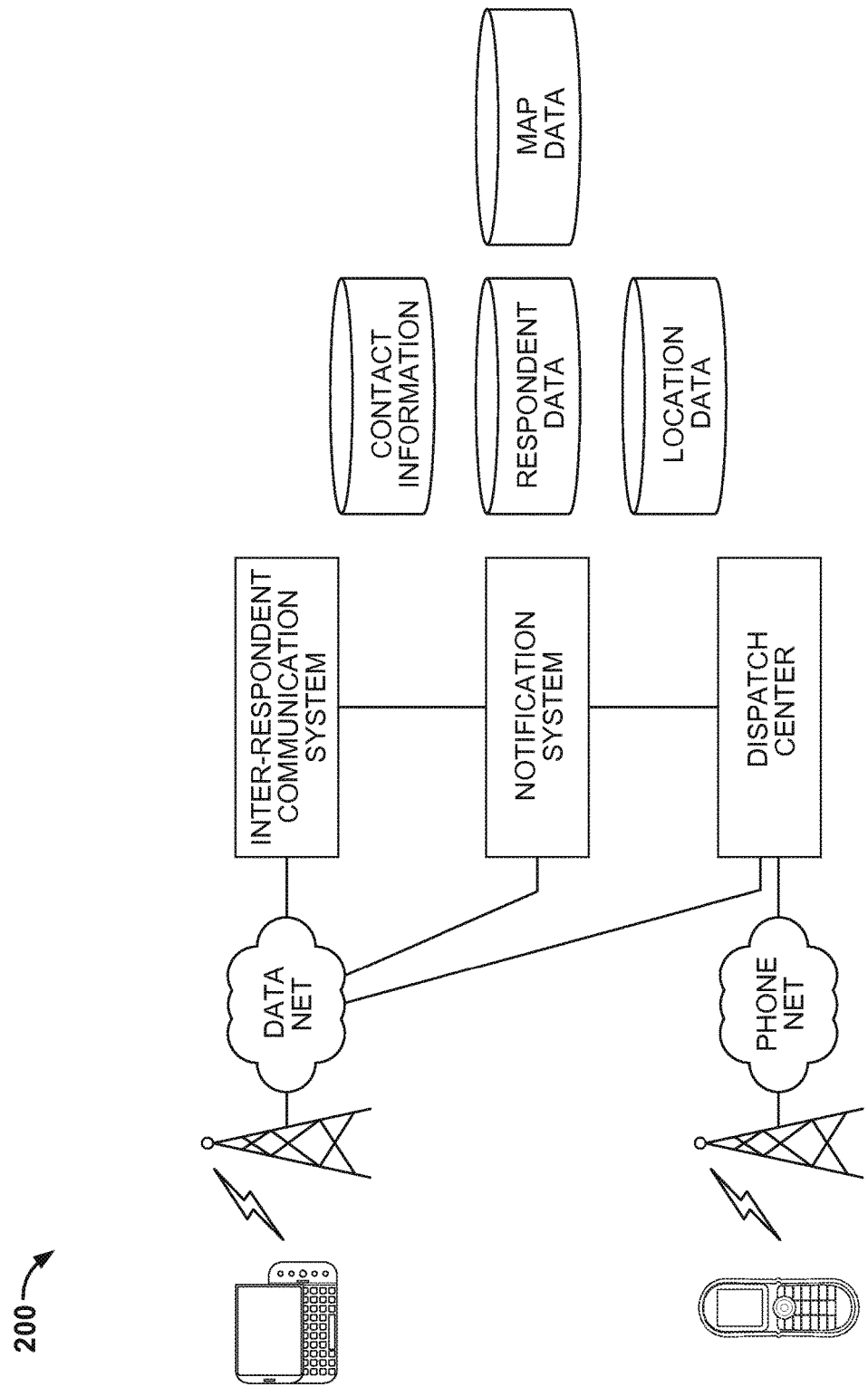
FIG. 2A is a block diagram of a system for coordinating lay response to emergency events.

FIG. 2A is a block diagram of a system 200 for coordinating lay response to emergency events. In general, the system 200 shows various main sub-systems that can be used in one example to implement functionality like that describe for FIG. 1 and below. The sub-systems are generally directed to receiving notification of an event that needs human responders, identifying lay responders in the area of the event, polling certain lay responders to see if they would like to be involved, and providing the lay responders who reply affirmatively with information to help them respond to the event. The sub-systems may also help coordinate the efforts of the lay responders with each other, and with professional responders such as EMTs or firefighters.

A central component of the system 200 is a dispatch center 202. The dispatch center 202 may be a traditional emergency 911 dispatch center where human operators receive calls about emergency events, take information on those calls, and notify appropriate professional responders so that they can respond to the calls. In this example, the dispatch center 202 is augmented with additional sub-systems to provide for greater functionality, including the dispatch of lay responders to emergency events. The dispatch center 202 may also be an automated system, separate from a manned dispatch center, that automatically identifies potential lay responders and invites them to participate.

The dispatch center 202 normally receives calls through telephone network 206 from basic telephones such as cellular telephone 222. Such reporting of events by telephone is old and well known and is not described in detail here. In this example, the dispatch center 202 may also be connected to a data network 204, which may include the Internet, so that the dispatch center 202 may receive data transmissions from, and provide data transmissions to, computing devices such as mobile computing device 220. The data network 204 may also be used to carry voice conversations between various components of the system 200, such as by using voice over IP technology. The dispatch center 202 may also bridge voice calls over telephone network 206 from telephone 222, to devices such as mobile computing device 222 communicating over data network 204.

Calls may also come into the dispatch center 202 via portable medical equipment worn by potential victims. For example, people who have had heart problems may wear the ZOLL Lifecore LIFEVEST wearable cardioverter defibrillator, which may monitor for cardiac arrest and provide treatment for the cardiac arrest. Such a device may also be provided with wireless communication capabilities so as to automatically report an adverse event, such as a cardiac arrest, for its wearer. Such a report may come in as a call to a dispatch system like dispatch center 202, and responders may be summoned in the manner described here. Alternatively, or in addition, a user of such a device may have previously specified particular lay responders in the event they have an adverse event, and such responders may be contacted automatically by a dispatch system when the device provides notification of an adverse event. For example, a user may provide telephone numbers for family members when they register such a device with a system, and the numbers may be automatically dialed, with voice messages automatically generated, when such an event occurs.

The dispatch center 202 may communicate in a traditional manner with an emergency communication system 203 so that the dispatcher can identify relevant professional responders who are assigned to cover the relevant area form which a call has originated, and to send those responders to respond to the call. For example, a dispatcher may cause emergency medical technicians in an ambulance to go on the call or may cause fire teams to deploy. Other responses may be orchestrated by the dispatcher according to the relevant standards of a particular dispatching office. In addition, the professional responders may be connected via voice and data with the other sub-systems described below, much in the same manner as lay responders, but the capabilities provided to the professional responders may be greater and more complex in character.

The dispatch center 202 may also communicate with a notification system 208, which is designed to provide notifications to lay responders (and professional responders) about emergencies that may be occurring in their area and for which their intervention may be requested. The notification system 208, in performing these operations, may initially serve as an interface between a dispatcher at the dispatch center 202 and various candidate and confirmed responders who are using devices such as mobile computing device 220.

The notification system 208 may also manage an enrollment process by which lay responders register themselves with the system 208 and are managed by the system 208. For example, the system 208 may track prior responses by lay responders to ensure that appropriate care has been given to victims, and may rate lay responders according to such tracking, so that certain lay responders may be identified as particularly adept responders and others may be lowered in rank on the system or removed from the system 208. Professional responders may also be rated or assigned to levels in a similar manner. For example, if a user confirms that they will respond to an event but then fails to respond, they may be removed from the system 208. The ratings may be used automatically or by a human dispatcher to select appropriate responders to invite to respond to a call. In general, as described here, a responder who is in the area of an event is referred to initially as a potential responder, a responder who is invited to respond is a candidate responder, and a candidate responder who replies affirmatively to an invitation is a confirmed responder. The system may treat each such category of responder differently, such as by providing map information and permitting voice communications only for confirmed responders.

The notification system 208, in performing its functions, may depend on and manage a number of sources of data. For example, location data 212 may be gathered from devices used by various responders who are enrolled with the system 208 to determine where the responders are located. Thus, for example, the notification system 208 may receive a query from the dispatch center 202 that identifies a location of an emergency and then use that location to identify enrolled responders who are currently in that same vicinity and whose devices are currently turned on and reporting their location. Such information may be made available voluntarily by the responders when they register with the system, so that they permit tracking of their current location for defined purposes and under defined conditions. Appropriate privacy controls may also be employed, such as by informing users before they opt into such a system, and providing indications that they have been "pinged" whenever such an operation occurs.

The notification system 208 may also store responder data 214. The responder data 214 may reflect various aspects of all responders who are enrolled with the system 208. For example, the responder data 214 may include identification data for each responder, such as the name and home address for each responder. The responder data 214 may also include contact information for each responder, including information needed to reach a mobile computing device that the particular responder is using, so that the responder may receive notifications about emergency events, and also information needed to establish a VoIP connection with the responder's electronic communication device. In addition, the notification system 208 may track performance of various responders, and may generate and store ratings or other similar information for each responder. For example, physicians who register with system 208 may be identified as a separate class of responders than ordinary lay people who lack specific medical training, or who have only CPR certification. Such information about the capabilities of responders may be provided, for example, to dispatch center 202 or to professional responders so that such users can see where trained professionals are in relation to an emergency event.

Map data 216 may also be stored by, or otherwise accessed by, notification system 208. The map data 216 may take the form of visual map tiles and data required to connect latitude/longitude coordinates or other such information to locations on the map. The map data 216 may also include data needed to generate navigational routes on maps, and also to convert English language (or other human language) addresses to more technical map identifiers such as latitude/longitude coordinates. While the map data 216 and other data are shown as being part of the notification system 208 in this example, they may also be accessed from other locations, such as from third-party services provided by companies like GOOGLE, YAHOO!, MAPQUEST, and MICROSOFT using API's that are public and generally familiar.

An inter-responder communication system 210 may be provided as an adjunct to the notification system 208. The inter-responder communication system 210 may be provided to allow voice communications between lay responders and each other, between responders and a victim, and between other parties that may be involved in an emergency response operation. For example, the dispatcher may use the system 210 to keep all responders acting in coordination as they move toward a scene. The inter-responder communication system 210 may access identifiers (e.g., telephone numbers, IP addresses, and the like) from the responder data 214 by which to create a voice communication channel between different entities in the system 200, or can access such similar information from contact information 218. Such connections may be made in familiar manners using existing technology, and could depend on systems such as GRAND CENTRAL, or GOOGLE VOICE.

The inter-responder communication system 210 may respond to selections made by a dispatcher, or by responders, in which one of the users is requesting to speak to one of the other users or to the entire group of users. The inter-responder communication system 210 may make appropriate voice connections between each of the users in such situations to carry out the stated intent of the requesting user.

As an example of the operation of system 200, a call may be initially received at the dispatch center 202 from telephone 222, such as through a 911 calling network. A dispatcher at the dispatch center 202 may speak to a caller on telephone 222 to find out that the caller is witnessing another person having a heart attack in the 600 block of Main Street. The dispatcher may begin to type information about the call into a computer terminal, including the text "500 block of Main Street", and such text entry may cause a map to be displayed on a computer display of the dispatcher, centered around the typed address.

The computer display may also show icons that represent all potential responders who are currently known to be in the area of the 600 block of Main Street (i.e., whose devices are on and reporting their locations). Such information may be obtained by the dispatcher's computer terminal by accessing information from the notification system 208, and then plotting icons for potential responders on the dispatcher's computer monitor. Each of the icons may be supplemented with a small indicator that shows the type of responder that each person in the area is, such as a trained physician or a relatively inexperienced giver of CPR.

The dispatcher may then select some of the identified responders in the area, such as by tapping their icons on a touchscreen computer interface, and may then select a control (e.g., click or tap an on-screen button) to have a notification generated for each of the selected responders, making them candidate lay responders. For example, in an urban area, the screen may show 20 or 30 lay responders in the general area of an event, and the dispatcher may use his or her judgment to select five or six of those responders as candidates for responding, and who will receive notifications of the event. (The particular respondents may also be selected automatically by the system, and the type and number of respondents selected, either manually or automatically, may depend on observations about the desired make-up of a response team and the likelihood that particular candidate respondents will respond affirmatively to an alert). Also, a dispatcher may broaden the area in which responders are sought or the category of responders who the dispatcher wants to have displayed, such as when a mass event is occurring or when an insufficient number of responders of a particular skill level show up in an initial area.

A system may also identify a mass event (e.g., a large automotive pile-up, chemical release, terrorist attack, and the like) automatically or with dispatcher assistance, such as when multiple calls come in from a particular small geographic region over a short time period. In such a situation, multiple dispatchers may be involved and responders may be assigned to multiple different teams, where each team may be assigned a particular type of task (e.g., traffic control, moving of debris, triaging of victims, treatment of victims, and the like). Where there are multiple dispatchers, the dispatchers may be assigned particular responsibilities and different levels of authority. For example, a lower level dispatcher may be able to assign rescuers to particular groups, but only upper level dispatchers may be able to move rescuers between groups or to define particular assignments for groups or individual rescuers.

In response to the dispatcher selection, the notification system 208 may be caused to send alerts to each of the candidate responders and their mobile devices, such as mobile computing device 222. The devices may generate an alert noise and/or visual indication. Some of the candidate responders may not reply to the alert, and after a predetermined time period, they may be taken out of the system as candidate responders. Other responders may respond in the negative, indicating that they are unable at the current time to respond to the call. Yet other responders may respond affirmatively to indicate that they would like to respond to the call, and such responses may be communicated back to the notification system 208. Those responders may become confirmed responders within the system 200.

The notification system 208 may then provide data for generating displays like that shown on the screen of smart phone 110 in FIG. 1, to each of the confirmed responders who indicated that they would like to be involved (and to the professional responders). The information may show the location of the caller that is using telephone 222. Where the location is uncertain, such as where the caller identified an entire block where he or she may be located, or where cell tower triangulation is used to find an approximate location for the caller, a map provided to the responders may show a colored circle that is approximately equal in size to the area of uncertainty of the users were victims location (similar to the uncertainty shown in the interface for GOOGLE MY LOCATION). As a result, the responders may immediately see that there is some uncertainty as to the location, and they will not expect to find the victim at a particular point, so they will be ready to search for the victim within the general area.

As confirmed responders begin to move toward the victim, their locations may be updated on each responder's respective device so that they can see where the other responders are, and identify whether they will be the first responder and also identify the other responders when they arrive. Such information may also be used by confirmed responders to determine whether they should divert to obtain equipment or other things.

Using inter-respondent communication system 210, the responders can also communicate by voice and/or text with each other and with professional responders to coordinate their activities. For example, one responder may tell the other responders that he or she is a trained physician and will take over certain responsibilities when he or she arrives at the scene. Such a communication may be comforting to the other responders and allow them to prioritize the sort of work that they will perform when they get to the scene. The responders may also communicate with professional responders who may identify the approximate time of arrival for themselves, so that the late responders may know how long they need to continue providing the victim with care.

The notification system 208 may itself, or in coordination with other sub-systems, track activities that happen during a response to an event and may provide for follow-up of the event. For example, the notification system 208 may track how many times certain responders are notified and how often they respond affirmatively, so as to provide the system 200 with data moving forward that can be used in determining how many candidate responders should be selected in order to obtain an appropriate number of real responders, and to determine which potential responders to identify as candidate responders (e.g., responders who never respond or who respond affirmatively but do not show up, can be demoted and not shown as potential responders).

Also, responders may be provided an opportunity, after an event, to post comments on the event so that operators of the system 200 can learn how to improve the system and the response to victims in the future.

The responders may also be contacted by the system 200 such as to provide them with tokens of appreciation, such as coupons for stores in an area around an event. In appropriate situations and consistent with patient privacy, the responders may also log onto the system later to be updated regarding the status of the victim so as to state their natural curiosity. At the same time, appropriate restrictions may be imposed so as to maintain the privacy of the victim and the responders. Certain responders may also have comments posted by the system to one of their social media pages (e.g., FACE-BOOK, TWITTER, or LINKEDIN) to congratulate the responder in a semi-public manner, which posting may include information to permits friends of the users register to become responders themselves.

Use of information about response events may also be stored and coordinated in a more systematic manner. For example, a rating module may review responder performance, which may result in a rating for a responder increasing or decreasing based on the abilities and responsiveness shown by the particular respondent. Such a rating can then be used by a human or automatic dispatcher in the future in determining which responders to change from potential responders to candidate responders.

The systems and techniques described here can also be expanded in a situation in which there are mass casualties, such as a large accident (e.g., train, bus, or airplane crash), a terrorist attack (e.g., bombing or gas dispersion), natural disaster (e.g., earthquake or large tornado), or public health crisis. For example, a system may initially determine manually, automatically, or semi-automatically, that a mass event is occurring, such as by determining that a number of calls for different events (e.g., different victims in need of held) over a time period (e.g., 1 hour) and in a particular area has exceeded a predetermine threshold. Such a determination may be made by using known automatic clustering analysis techniques so as to distinguish calls that are connected as shown by time and geographic location, from those that are independent but happen to be spatially and time related. Upon the condition of a mass event being recognized, the system may generate an alarm to begin elevating the status of the event. For example, the alarm may first be provided to a dispatcher or dispatchers who may attempt to confirm the nature of the event, such as by asking a caller at the scene a series of questions designed to elicit information about the type of event and scope of the event (e.g., "Is your breathing painful?", "Are other people around you having problems?"). At a next stage, a mass disaster response procedure may be triggered, by which appropriate agencies are informed of the event, and proceed according to pre-established procedures.

In addition, responders on the scene may capture and automatically upload digital photographs that may be geo-tagged automatically and provided on a display like that shown in FIG. 5A. In particular, icons for each of the photos may be displayed on a map (such as provided by GOOGLE MAPS) and indicating the direction the photographer was facing. Such images may, when they cover an adequate area, be combined, such as using the MICROSOFT Image Composite Editor. Central administrative staff may then use the images to get a better feel for the situation on the ground.

First responders may also be able to provide meta-data for the system, that may be used by later responders. For example, mass events can result in great traffic problems and confusion as rescue vehicles arrive on a scene and interfere with each other. A first responder could be assigned by a dispatcher to survey the area around the event, identify a large enough flat area for parking and staging of victims, and identify a traffic pattern for vehicles entering and leaving the area (which may be contrary to the standard traffic flow in the area). For example, the first responder may identify a large, partially-filled parking lot off a one-way street, order a tow truck to remove the few cars in the lot (where the dispatcher may affect the notice to the tow truck company) and define that half of the lanes on the street be designated as flowing the other way. Such information may then be added to a map of the area, and the map may be presented on displays in fire trucks, ambulances, and other vehicles so that the drivers of those vehicles can quickly find the staging area and do so without blocking each other.

The systems and techniques may also be used to coordinate responses to such mass events. For example, lay responders and professional responders may be assigned to particular portions of the event, such as particular victims or groups of victims. Thus, for example, a navigation aid to professional responders may show the responders where, within a larger area, they are to go, so that dispatcher and other administrators may directly organize and place assets at an emergency site. Responders may also be grouped according to a sub-part of the event, and each group of responders may simply see others in their group on their communications devices, and may connected by voice only to the members in their group. Use of VoIP connecting in this regard may make such grouping relative simple and convenient. On the dispatchers' terminals, the groups may also be represented distinctly from each other, such as by making icons for the responders in each group a color that is distinct from responders in another group. In this manner, the dispatchers can see quickly whether group members are working in coordination (because they should be grouped on a map), and can directly speak to any responders who do not appear to be in the right location, and find out why they appear to be out of position.

The tracking and storage of data like that discussed above may also be particularly important for mass events. Specifically, mass events do not happen very often, so there are few opportunities to study them and improve on the manner in which rescue services respond to such events. Location tracking information and stored audio files of responder conversations may, in this regard, provide a valuable tool for researchers who are trying to better understand such situations and improve on responses to such events.

In addition, certain responders may be tasked with registering the identities of victims of an event. Such information may be used for follow-up purposes, such as to track the subsequent health of victims, to provide compensation to victims, to identify potential witnesses to relevant events, and the like. Such registration by first responders may be particularly beneficial when typical mass event follow-up personnel cannot get to the site quickly, and thus may miss witnesses or victims who left quickly. As one example, dispatchers may assign particular responders to form a perimeter around an event and to log individuals who leave the perimeter. The information gathered about individuals at the site of a mass event (e.g., a hurricane) can also be used for generating mass statistics, such as for reporting the severity of a mass event.

Figure 2B:
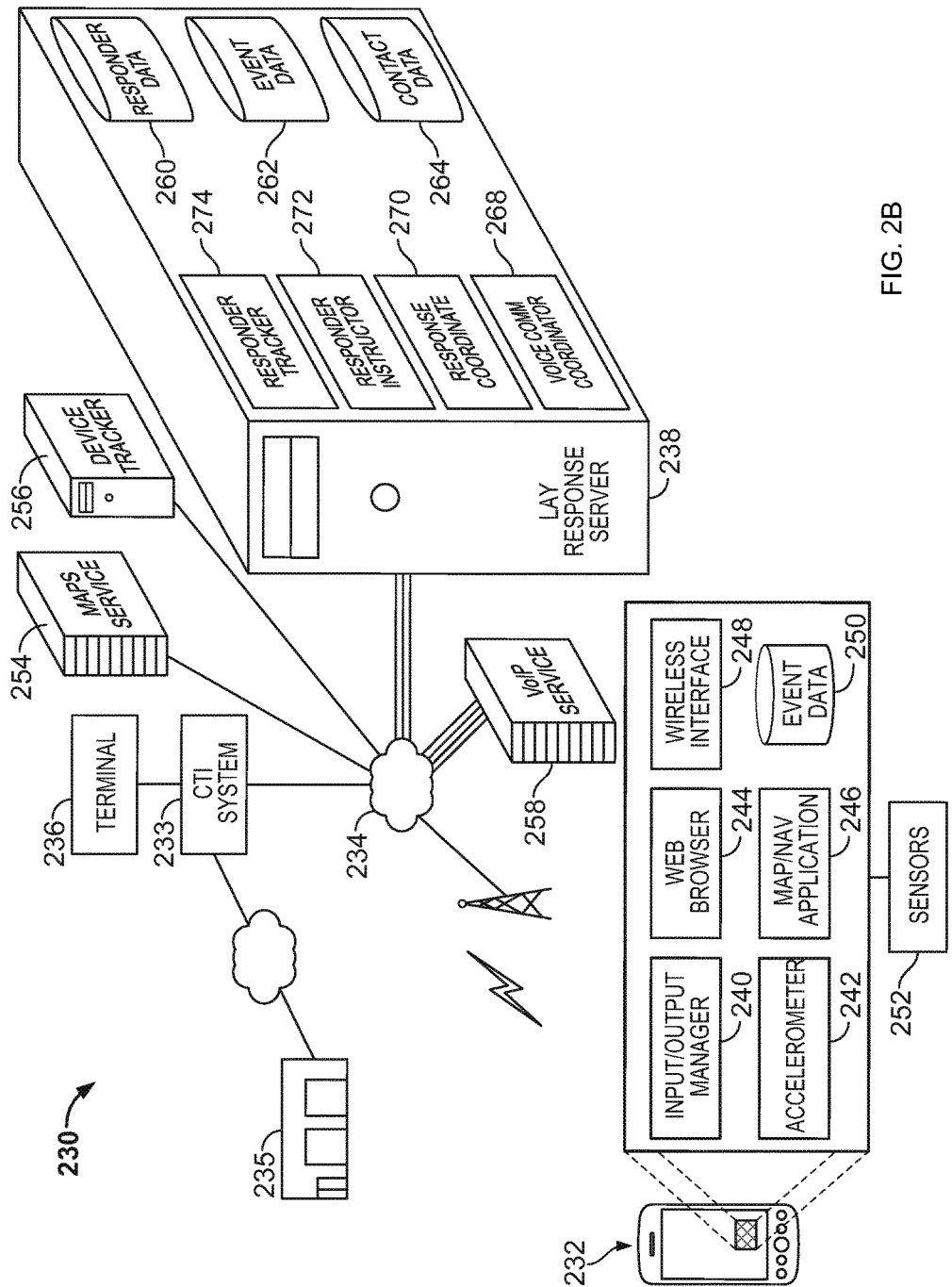
FIG. 2B is a block diagram of a system having a number of sub-systems for coordinating lay response to emergency event.

FIG. 2B is a block diagram of a system 230 having a number of sub-systems for coordinating lay response to emergency event. In general, the system 230 may be arranged and programmed to provide functionality like that described above, though additional details are shown here for components that can carry out the functionality.

In this example, the system 230 includes a number of components to communicate through one or more networks such as the Internet 234. For example, a mobile computing device 232 may be used by a number of lay responders or professional responders to receive information about emergency or similar events, and to respond to the events. Various components within the communication device 232 may provide for such functionality, and may include components that are normally part of the device, or components that may be added to the device later by a user.

One such component is an input/output manager 240. The manager 240 plays a normal role in the device, including by managing the manner in which graphical components are displayed on a screen of the device 232, and receiving input from a user of the device 232, such as on a touchscreen, trackball, and physical or soft buttons. The manager 240 may, for example, determine where on a touchscreen display a user has selected, or where a selection with a pointer has been made, in coordination with what is being displayed on the screen, in order to determine commands and other input that a user is providing on the screen.

An accelerometer 242 in the device 232 senses relative motion of the device 232. In implementations where the device 232 is fastened to the hands of a person performing CPR chest compressions, acceleration sensed by the accelerometer 242 may be double-integrated and otherwise processed to produce a measure of the displacement of the device in a vertical direction. Such displacement may closely approximate the level of displacement of a patient's chest during the chest compressions, and may be reported to an application of the device and communicated to other components in the system 230.

A web browser 244 may be included with the device 232 and may receive content from remote services that is formatted in known manners for display on the device 232. The web browser 244 may support the transmission and display of rich content, so that a user may interact with the content in manners like those discussed above for FIG. 1. A map/navigation application 246 may be provided as part of the web browser to display content downloaded to the web browser 244, or may be a separate stand-alone application on the device 232. The map/navigation application 246 may receive location information from remote services, and from device 232, such as from a GPS module that is part of device 232, may generate a map that may be overlaid with navigation information, and may also provide turn-by-turn navigation as a user moves toward an emergency event.

Wireless interface 248 may provide for data and voice communication with a network in a familiar manner, so that a user of device 232 may talk to other responders heading toward an emergency event, and may also provide and receive data describing the event and actions occurring around the event. An event data store 250 may save information regarding actions taken by a user of the device 232 around the time of an event, such as information from accelerometer 242, and information from other sensors 252. The other sensors 252 may be part of the device 232 itself, such as light sensors or a touchscreen of the device 232, or may be sensors that are provided as add-ons that may communicate with the device 232 through a wired or wireless connection. For example, a user of device 232 may purchase an electronic stethoscope that may plug into device 232 and act as a traditional stethoscope. A user may also purchase a blood-pressure cuff or other such sensors that may provide electronic signals to device 232 so that readings of victim parameters, and particularly vital signs, may be uploaded easily to the rest of the system through the network 234.

Separately, a CTI computer/telephone integration system 233 may be provided at a dispatch service, and the CGI system 233 may communicate information to a terminal 236 that is used by human dispatcher. The terminal 236 may include a computer monitor and keyboard, in addition to a telephone headset that the dispatcher may use. The CTI system 233 may integrate information like that discussed above and below, including voice information from incoming calls and from responders, and data that represents information about a call and operations occurring in the geographic vicinity of the call. Such information may be used by a dispatcher to direct rescue teams and lay responders to the call. Alternatively, the dispatcher may pass responsibility for coordination of a call to another administrative user so that the dispatcher may return to receiving new calls, and the other user may stay with a particular call for a longer time.

The CTI system 233 may also be connected to a professional response facility 235, such as an ambulance garage or fire station. Such a connection may allow a dispatcher to trigger an alarm so that emergency safety personnel are dispatched to a call. Information from the system 233 may be downloaded automatically to the facility 235 and also to a vehicle that is responding to the call for the professional responders.

A lay response server 238 may coordinate notifications to potential lay responders, responses from the responders, and management and coordination of the responders when they respond to an event. For example, a responder tracker 274 may be programmed to obtain GPS or other data regarding the electronic communication devices for users who are registered with the server 238. Such data may be obtained directly by the server 238, or may be obtained by querying a device tracker 256 (e.g., which may be operated by a wireless service provider for devices on the provider's network), which specializes in obtaining such data. A responder tracker 274 may normally not track locations of users, and may simply check the locations upon being notified by the CTI system 233 or another source about an emergency event in a particular area. When such a notification occurs, the responder tracker 274 may obtain the locations of registered users, and may pass on to an appropriate sub-system only the locations of users that are within a predetermined distance of an event.

A responder instructor 272 may be responsible for generating instructions for responders who have been identified in a particular area by the system. For example, the responder instructor 272 may, be provided with the identity of particular responders in an area, and may deliver preformatted requests to the responders, inviting them to respond to an event in the area. A responder instructor 272 may also later provide instructions by voice or in typed form, to help coordinate the response of responders who agree to move toward the event.

A response coordinator 270 may track the location and actions of various responders in the system, and may provide instructions to the responder instructor 272 and further coordinate such responses. For example, the response coordinator 270 may determine that a particular responder has picked up a defibrillator on their way to an event, and may thus instruct other responders that they need not do the same thing. For example, such instruction may be provided by adding an icon or a defibrillator to an icon of a particular user to be shown on the displays of various responders' devices. Such instructions may also be more explicit, and could be typed or spoken by the responders' devices.

A voice communication coordinator 268 may be directed by other components of the system, such as response coordinator 270 to identify information for connecting responders for voice communication, and initiating such connections, such as through VoIP service 258. For example, the response coordinator 270 may receive a message from the device 232 in response to a user clicking a "talk" button on the device, and may cause voice communication coordinator 268 to have a voice connection made between the user of device 232 and another responder, other responders, or a dispatcher. The voice communication coordinator 268 may send commands to the VoIP service 258 in order to effectuate such connections.

Various data sources may be used by server 238 (which may be one or more servers acting together in a system). For example, responder data 260 may include information identifying registered responders for a system, history data regarding responses made by each responder, ratings data for each responder, and the like. Event data 262 may include data, organized by each emergency event for which the server 238 coordinated a response, that reflects some or all of the data collected by responder devices and passed through the system, including vital sign data collected by responders, data showing the paths of responder, and audio files of voice communications between and among responders.

The event data 262 may be stored for a large number of events, for research purposes. For example, research may access data showing arrival times and responses for different events, and may make conclusions that permit for adjustments in the ways that dispatchers handle events. For example, different types of responders may be determined to make up a better response team, or different sizes of teams may be used. Also, such information may be used to determine how many responders need to be invited to respond to an event in order to get an appropriate number of confirmed responders.

More general clinical research may be conducted on such data. For example, researchers may conduct studies on the sorts of emergency response approaches that lead to the best outcomes, by combining the event data 262 with outcome data for patients who were treated by the events. For example, such research could establish that use of particular types of lay responders either improves or degrades a victim's chance of survival from certain emergency events such as cardiac arrest. Also, outcomes may be compared with respect to whether certain equipment such as portable defibrillators was made available to a victim, and when such equipment reached the victim.

Figure 2C:
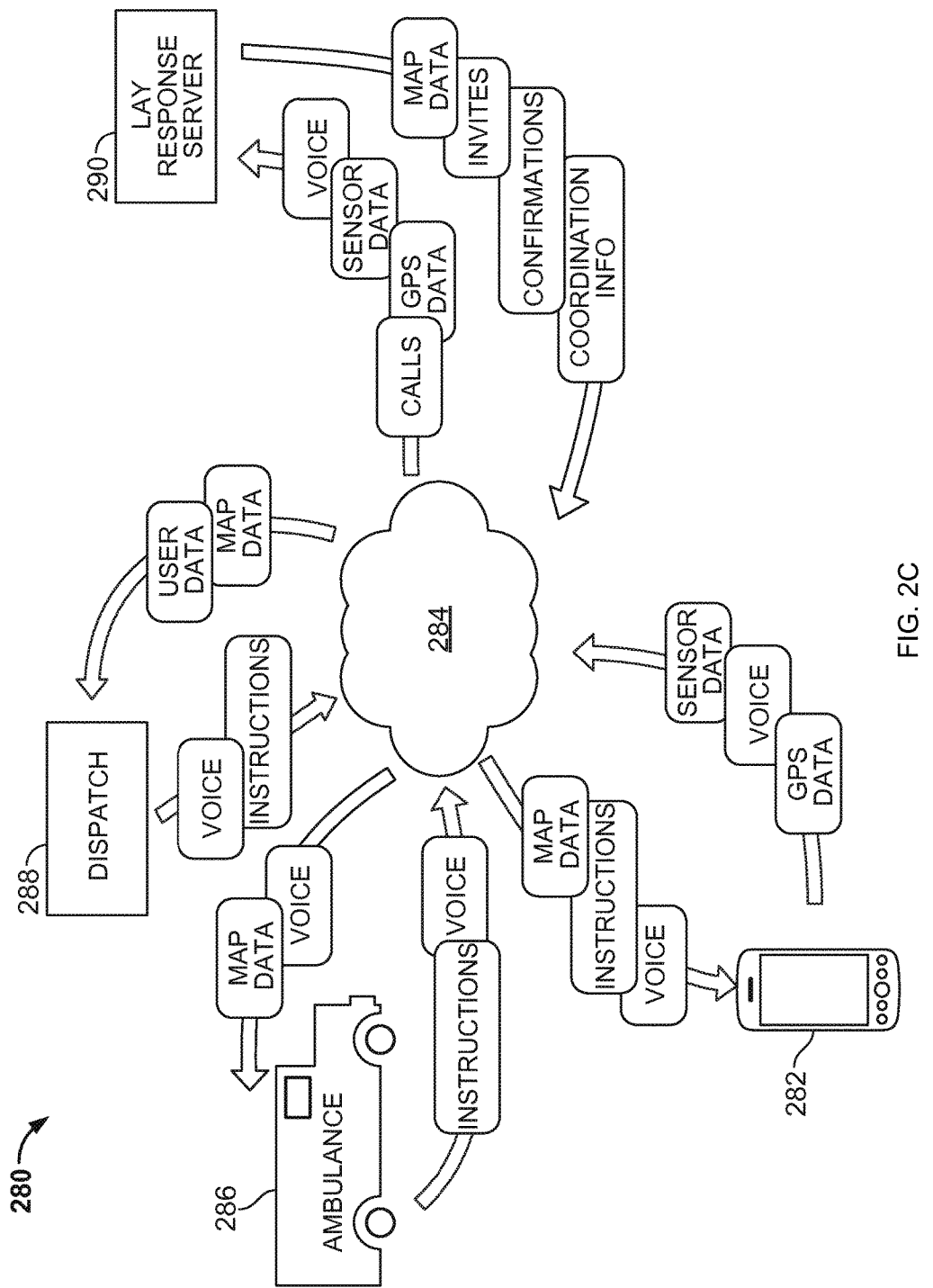
FIG. 2C is a block diagram showing example information flows between sub-systems in an emergency response system.

FIG. 2C is a block diagram showing example information flows between sub-systems in an emergency response system. The particular components shown here are sub-sets of those shown in the prior figures, and the focus is instead on example types of messages that may be passed between or among the components, through one or more networks 284 such as telephone and/or data networks.

A first component in this example is a dispatch system 288. The dispatch system 288 may be a traditional dispatch system that has augmented functionality for directing lay responders to an event. The system 299 may generated, for example, voice streams of a human dispatcher who is trying to direct lay and professional responders, and to respond to a caller who called in an event. The dispatch system 288 may also provide instructions in the form of data that a dispatcher may type into a terminal, including address information for an event. The dispatcher may also be provided with a map like that shown in FIG. 1 or FIG. 6A, soothe dispatch system may receive user data and map data in order to generate such a display.

A lay response system 290 may be responsible for notifying lay responders about an event, as triggered by the dispatch system 288, register such responders initially, coordinate the response by the responders and other similar functions. The lay response system may generate information for coordinating a response, may provide confirmations to lay responders to indicate that they are confirmed responders, invitations to lay responders, and map data for generating displays like those shown above. The lay response system 290 may store and respond to a variety of data types that it receives, including direct emergency calls, GPS data showing the locations of responders and victims or calls, sensor data from electronic devices used by responders, and voice communications between and among callers, responders, and dispatchers.

An emergency response vehicle 286 may contain a familiar portable computer system, and may permit crew members to provide typed instructions and voice communications to other parts of the system including to lay responders, The vehicle 286 may receive, in turn, map data that shows their location and the location of the victim, along with locations of the lay responders. The vehicle 286 may also receive voice communications from the dispatcher and the lay responders.

A responder client communication device 282 may be used by each of the various responders and may take a variety of forms, but may generally be provided with telephony functionality, and preferable web-based data access and display functionality. The device 282 may also be arranged to download and execute custom applications from an app store, in some circumstances. The device may provide to other components data that includes GPS data, voice communications from the user of the device 282, and sensor data from the device, such as data sensed by a touch screen on the device (e.g., to obtain a victim's pulse). The device 282 may in turn receive a variety of information such as voice communications from other parts of the system 280, instructions such as those provided by a dispatcher or professional responders, and map data.

Figure 3A:
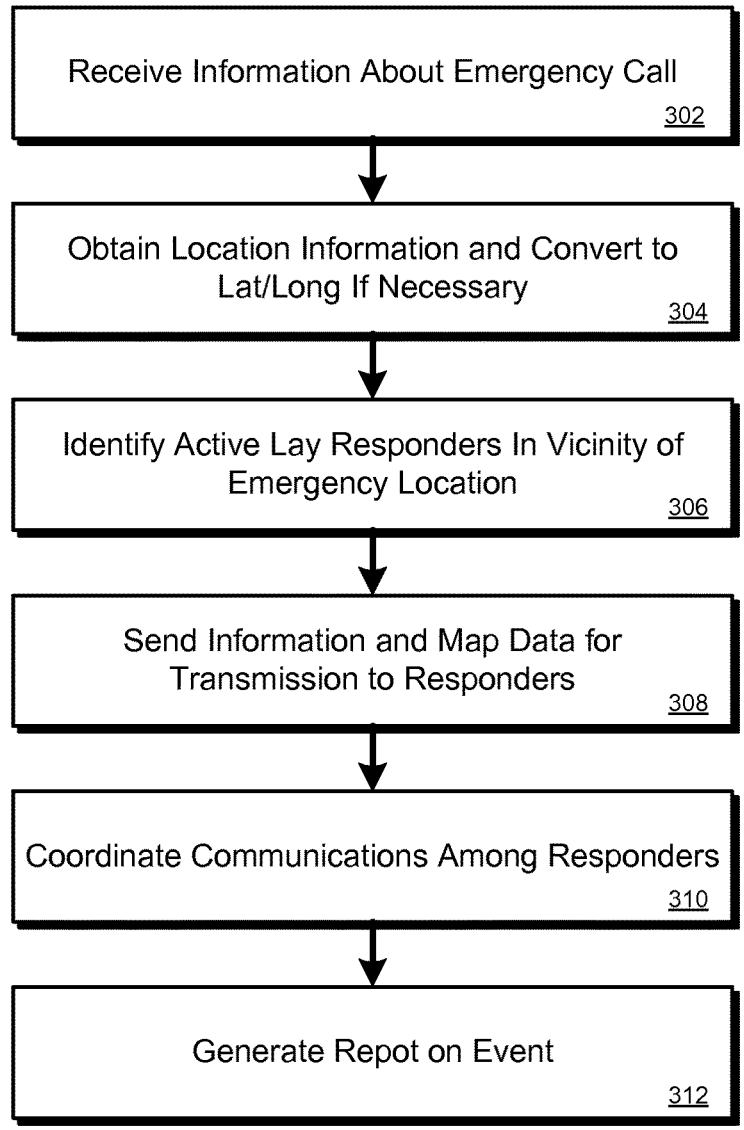
FIG. 3A-B are flow charts of processes for organizing responders to an emergency call.

FIG. 3A is a flow chart of a process for organizing responders to an emergency call. In general, the process involves identifying a number of law respondents who have registered with a system and are in the vicinity of an incoming emergency event. The process then tracks the actions of responders as they approach the event and attend to a victim or victims at the location of the event.

The process begins at box 302, where a system receives information about an emergency call. In one instance, the call may be a 911 call and the information may be entered into a computer terminal by an operator who answered the call. In other instances, the call may be a data transmission from a mobile computing device. In either situation, a location for an emergency event may be determined, such as by the operator typing in an address relayed by the caller, or by location information received with a data transmission (e.g., GPS data from a mobile computing device). The information may also include contact information for the caller, such as an IP address or email address for a mobile computing device, or a telephone number (e.g., determined using an automated number identification (ANI) service). Such contact information may be used later to allow responders to speak with the caller, including by patching such communication through a network associated with the dispatch system.

At box 304 a geographic determination component of a system obtains location information like that discussed above and converts it to a latitude/longitude coordinate or area. For example, a dispatcher's terminal may provide for parsing of text that the dispatcher types and any addresses that are identified in the text may be passed to a separate system that may turn the address into a latitude/longitude coordinate. In response, another system may be caused to transmit data to the dispatcher's terminal so that a map of the area around the event is displayed to the dispatcher.

At box 306, active lay responders in a vicinity of the emergency location are identified. For example, the same system that transmitted the map data to the dispatchers terminal may also access a tracking sub-system that is aware of or can poll the locations of mobile computing devices for all people who are registered as potential responders with the process, who are in the vicinity of the emergency, and who have their devices turn on, reporting their current location.

The possible responders may be determined based solely on distance from the event, such as by circumscribing a circle of a particular radius around the event (where the circle can be made larger and larger until a predetermined number of potential responders can be found). Responders may also be identified separately based on the type of responder they are. For example, the 10 closest CPR-certified responders may be identified along with the three closest physicians, even if the physicians are farther than any of the lesser trained responders. Also, responders may be selected based on their estimated time to respond, so that a system could look at the current speed of a responder to infer that the responder is in an automobile, and thus could arrive at the event more quickly than a responder who is not currently moving. Also, mechanisms may be provided in smart phones so that the devices can report on whether they are docked into an automobile, so that the system can infer that users of such devices are able to travel farther than other users to respond to a call. In addition, the smartphones may have tools, such as real-time CPR feedback, or content that would better enable responders to assist victims of an event. The type of communication device and whether such tools are available on the device could also be indicated on a graphical display to a dispatcher.

At box 308, the process sends information and map data for transmission to responders, and particularly to lay responders. (Professional responders may be contacted in the same manner or may be contacted in a traditional manner.) The information may include some basic information about the emergency and also information needed to generate an annotated map like that shown in FIG. 1.

At box 310, the process coordinates communications among the responders. As described above, for example, the responders may be connected to each other in a form of walkie-talkie party line communication so that they can coordinate their approach to dealing with the emergency and to make sure that they are not preparing to perform redundant operations.

At box 312, the process generates a report on the emergency event. Such a report may be generated after the victim is indicated as being picked up in an ambulance or being admitted to a hospital, or the event has otherwise terminated (e.g., if it was a false alarm). The report may include various types of data gathered during the response, including data showing motion of the various responders, equipment picked up by the responders (to ensure that the equipment finds its way back to the rightful owner), audio transcripts of the communications between and among the responders, application of tools such as CPR feedback and CPR data, and the like. In addition, notice of the report may be sent to each of the responders (e.g., in an email with a hyperlink that aims at the report) so that they can review it and comment on it.

Figure 3B:
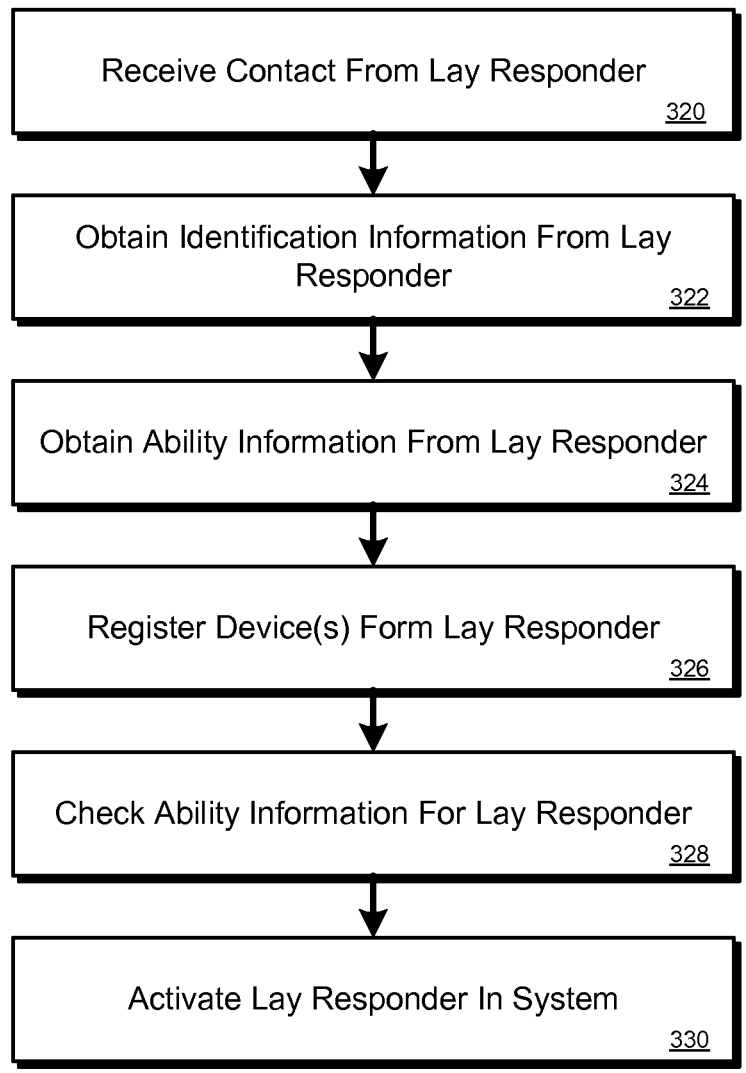

FIG. 3B is a flow chart of a process for enrolling a lay responder with an emergency response system. In general, the process involves obtaining identification information from a person who wants to be considered as a responder when emergencies around that person occur, and potentially of verifying the ability of the person to be a responder.

The process begins at box 320, where contact from the person wanting to be a lay responder is received. Such contact may be by the lay responder visiting a sign-up web page at an appropriate web site. The contact may also occur when a user downloads a particular application from an on line app store, and the applications causes the contact to be made. For example, a CPR training application may allow a user to practice CPR and have their progress tracked by an accelerometer in their smart phone (where they strap the phone to their hand as they perform CPR on a foam block or a dummy). The training may also involve the user reviewing training materials and taking and passing one or more tests or quizzes. When the user has demonstrated proficiency, the application may offer the user the opportunity to be registered as someone who has at least minimum competence to perform response and rescue activities.

At box 312, identification is received from the lay responder. Such information may be provided manually by the lay responder or may be acquired automatically from a contacts database stored on the lay responder's mobile computing device or from an on-line account that corresponds to the lay responder. The information may include the responder's name and address, employer and job title, and telephone number and email address among other things.

At box 314, the device for the lay responder is registered. Such registration may simply involve obtaining adequate information about the responder or the device so that the process can know where to send subsequent alerts to help ensure that they will reach the responder.

At box 316, the process checks ability information that the lay responder has provided. For example, the process may simply check to determine that the responder has successfully passed the testing that may have been imposed by the application that the responder acquired from the app store. For higher levels of confidence, such as when the responder reports that he or she is a physician, the process may follow standard identity verification techniques, such as by contacting an employer identified by the respondent and having the employer confirm that the respondent is who he or she say they are. Upon the confirmation, the respondent may later be identified to other users of the system, such as dispatchers and professional responders, as having that particular skill level.

If the responder checks out, they may be activated in the system (box 330). Such activation may involve providing the responder with various warnings and obtaining agreement that the responder's location may be tracked for purposes of identifying the responder as available to respond to an emergency event. Other appropriate affirmations may also be sought and received from the responder before the responder is activated with the system. Activation in the system may involve adding an identifier for the responder to a portion of the system that generates alerts, and subsequently tracking the responder's location when information about that location is available to the system.

Figure 4:
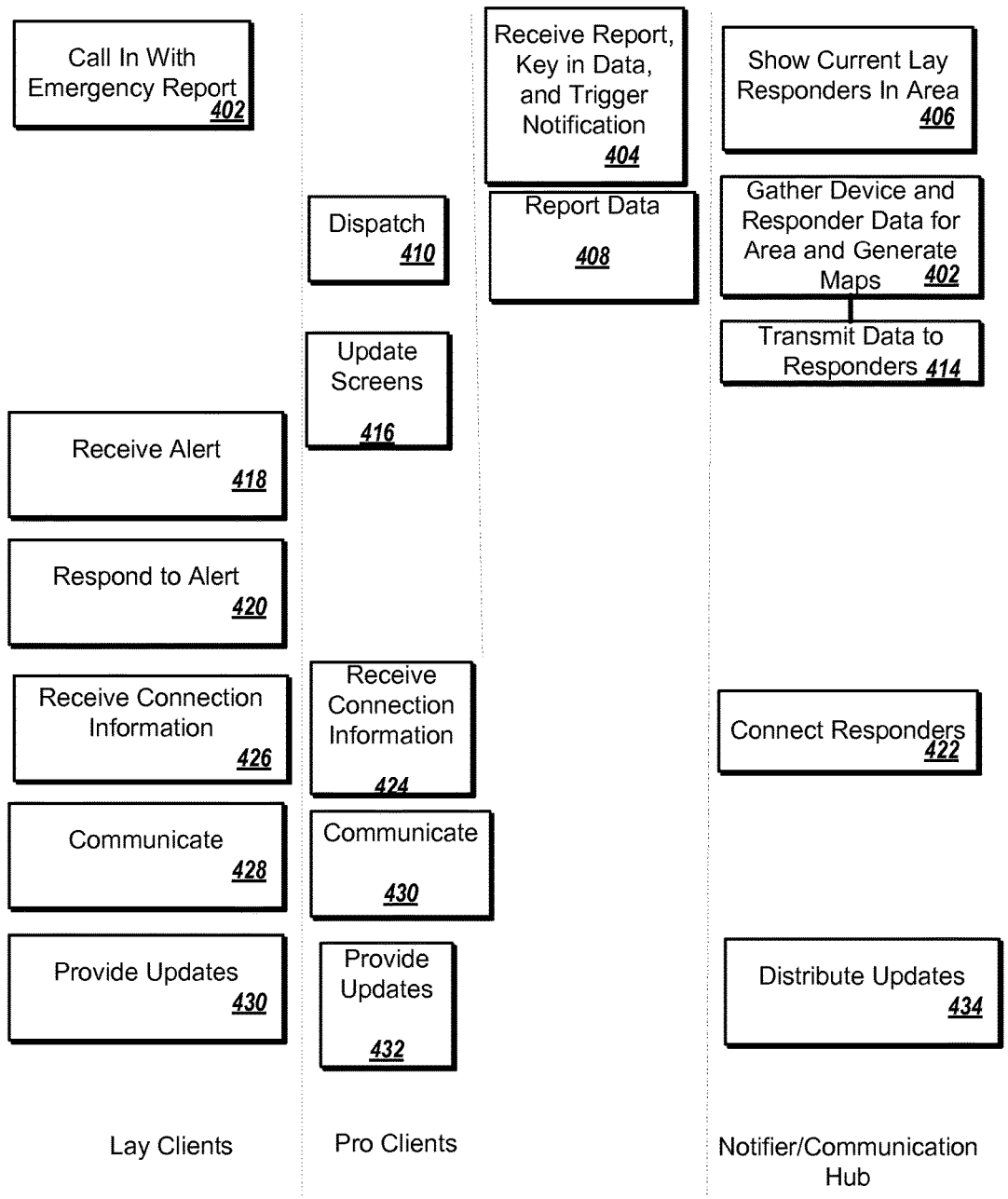
FIG. 4 is a swim lane diagram of a process for providing different types of responders to an emergency event.

FIG. 4 is a swim lane diagram of a process for organizing responders to an emergency call. FIG. 4 generally shows an example of actions that may be performed by particular components in processes like those discussed above, where location information is entered into the process manually by a dispatcher.

The process begins at step 402, where a client device (where a client is generally a device for a particular user, and a server is a device that provides information to multiple client devices), such as a telephone, calls into a dispatch service to report an emergency that is occurring. The dispatch service receives a report at box 402, the dispatcher keys in the data reported by the caller, and the dispatcher causes a notification to be triggered. Before triggering the notification, the dispatch component may communicate with a notifier/communication hub to determine whether there are lay responders in the area, how many there are, what type of lay responders they are, and how close they are to the location of the caller. In addition, the dispatcher may determine whether to trigger a notification to lay responders in any event, for example, if professional responders are sufficiently close to the location that lay responders would not provide much additional benefit.

At box 408, the data acquired by the dispatcher, which may include data representing a location of the caller, may be reported out, both to the client devices of professional responders, at box 410, and to the hub at box 412. The professional responders may dispatch in a conventional manner and begin heading toward the event, while the hub may gather device and responder data for the area around the reported event, and may generate maps for the various responders.

At box 414, the hub transmits data to the responders, including professional responders and candidate lay responders that were identified by the dispatcher or by an automatic process. This data may include data required to generate maps on the client devices of the lay and professional responders. At box 416, the professional clients update their screens, under the assumption that they previously were displaying screens generated from their standard dispatch that already showed them the location of the event.

At box 418, the client device for the lay responders (the lay clients) receive an alert notifying them about the events. At this stage, each of the lay responders is a candidate responder and has not yet agreed to respond or declined to respond. At box 420, each of the lay clients responds to the alert, and in this instance, only the affirmative responses are shown. (The system may also receive negative responses or non-responses, and would remove such responders from consideration for this particular call.)

At box 422, the hub connects the various responders to each other for communication. For example, the communication may be by visual data on their devices, such as by updating, on each responder's map, the location of the other responders. The communication may also be by voice, such as by the hub providing a voice over IP connection between all of the various responders. At box 424, the professional clients receive the connection information, and at box 426 the lay clients receive the connection information. The clients may use that information to establish the various necessary communication channels, such as by establishing voice over IP links between each other, or between each client and the hub.

At box is 428 and 430, the various responders communicate with each other to coordinate the response to the event. Throughout the response, the hub may distribute updates, at box 434, to the various responders, and the responders' clients may provide them with the updates as shown by boxes 432 and 430. The updates may take a variety of forms, such as the hub providing new information about the event. For example, the hub may obtain information about a car accident and may learn that, instead of an initial single victim (as initially reported to a dispatcher), there are actually three victims. (For example, a second caller at the scene may have dialed 911 and provided more accurate information than did the initial caller.) This information may be used by the responders to better plan their response to the event. For example, the responders may agree to spread out, with one lay responder attending to each of the three victims, and also later-arriving responders may be told which victims have been covered by earlier responders so they the later responders can immediately attend to victims who have not yet received attention. The hub may also inform the responders of other steps that have been taken, such as the calling of an ambulance, of a second or third ambulance, a fire truck, or other actions that may need to be taken, and that should not be taken more than once or otherwise occupy the time of the responders.

Although in the early steps of the process discussed here, the information about an event's location came verbally from a caller, such information may also be obtained automatically, including by a system that does not use a human dispatcher. In particular, a called system may use information to identify a general location for a caller using tower triangulation methods such as MY LOCATION. Such a system may also be contacted by an application on a device, and the application may cause longitude and latitude components for a communication device to the system (e.g., as determined form a GPS module on the device). The determined location may then be fed automatically into a process that seeks out a list of potential responders within a defined area of the event, and generates data for producing maps that show the area around the event, the responders in the area, and potentially response equipment in the area.

Figure 5:
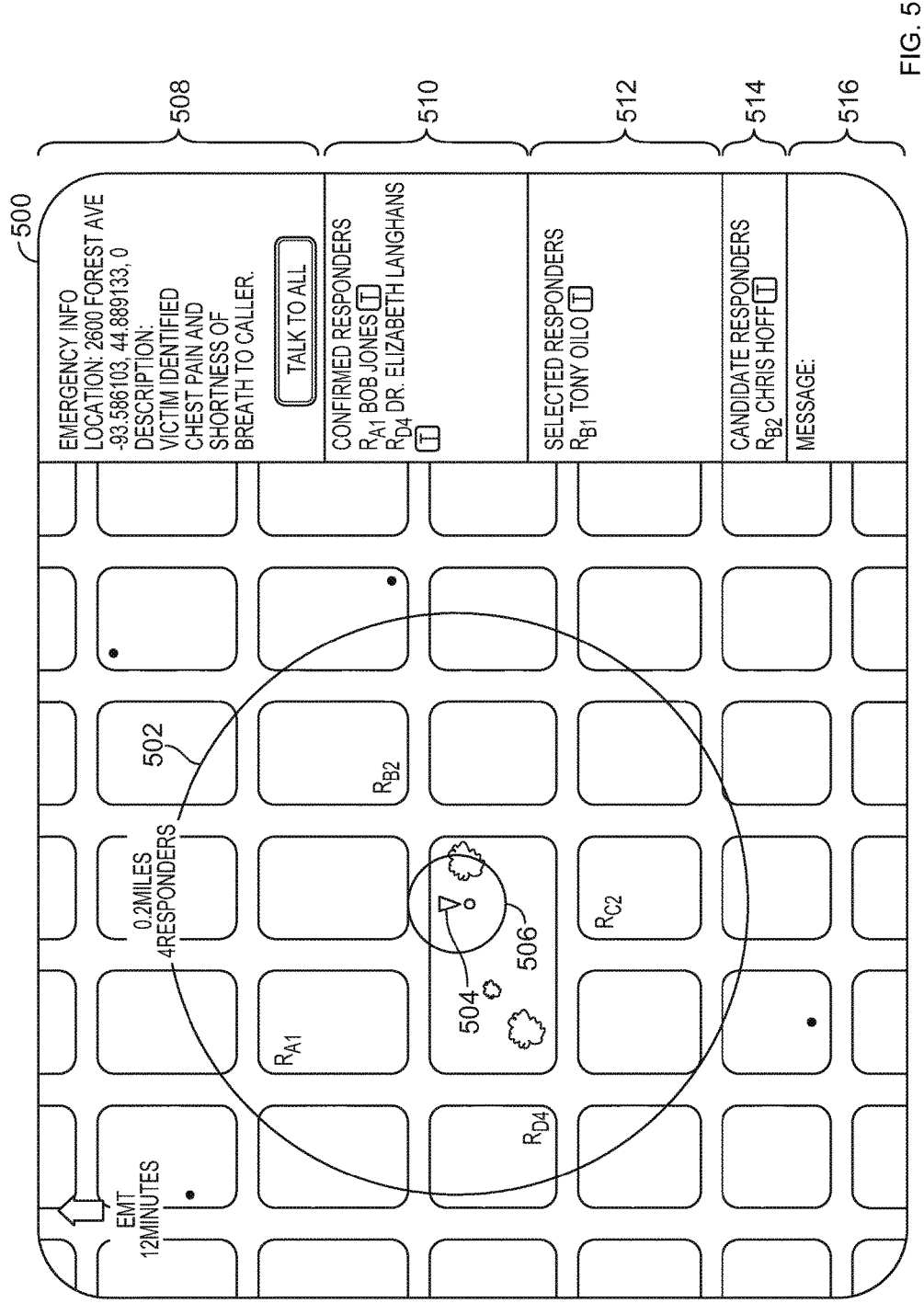
FIG. 5 shows an example screen shot for a dispatcher.

FIG. 5 shows an example screen shot for a dispatcher. In general, this screen shot provides an example of the type of data a dispatcher may see as the dispatcher selects lay responders to respond to an emergency event that has been called in by telephone.

The screen in this example is split mainly into a map area and a data area. The map area is centered around a victim represented by icon 504, and may have been retrieved automatically as soon as the dispatcher typed a location into their computer terminal. A circle 506 may be shown around the icon for the victim, showing a zone of uncertainty for the victim's location, which may be brought on because the caller's communication device does not have precise location capabilities (e.g., their GPS could not work in a dense city and tower triangulation is imprecise). A broader circle 502 indicates a candidate zone around the victim. This circle may circumscribe the area within which the system will look for potential lay responders, and the size of the initial circle may be selected automatically, such as to be a predetermined radius, or based on estimated time for lay responders to arrive at the victim. For example, real-time traffic data may be obtained by a system to determine how long it would take a lay responder to get from one location to another, or time for the lay responder to run to location may be determined (such as by plotting a hypothetical travel path for the lay responder). If the dispatcher does not see enough lay responders in the circle, the dispatcher may provide an input to change the size of the circle, such as by dragging the circle in or out on a touch screen display.

In the data apportion of the screen 500, and at the top, there is shown an emergency information area 508, where various data about an event may be displayed, such as the location of the victim (in plain English and lat/long), and a description of the event that the dispatcher may have entered upon receiving a call. Such a description may then be sent automatically to any responder that becomes confirmed in the system, or even to potential responders in an invitation. The area 508 also includes a selectable button that, when the dispatcher presses it and holds it down, causes the dispatchers speech to be broadcast to all responders (e.g., all confirmed lay responders and all professional responders), such as when the dispatcher wants to broadcast instructions to the team. Other similar controls may also be provided as needed.

A messages area 516 at the bottom of the data area provides a location in which a dispatcher can enter textual messages to be sent to the responders. Other data input and output may also be provided in one or more pop up boxes that may appear depending on the context of the system that the dispatcher is controlling.

The three remaining areas of the data area indicate the status of various lay responders in an area, coordinated with icons on the map area that show those lay responders. For example, in this display, candidate responders area 514 shows responders in the relevant area who have not yet been acted on by the dispatcher. Here, there is one such responder named Chris Hoff, who is designated with a B2 subscript, indicating that he is the B responder on the map and he is a level 2 skill level, which may be a lay responder who is formally CPR certified. A "T" icon is shown next to his name, and the dispatcher may select that icon in order to talk by voice directly with him; the dispatcher could also push the icon and then type a message, and that message would be sent directly to Mr. Hoff.

The selected responder's area shows responders who have received an invitation to respond. A dispatcher may move someone from area 514 to area 512 by selecting their entry and then dragging it upward from one area to the next. Here, the dispatcher has selected a level 1 responder, which may be someone who has shown proficiency for CPR with a downloaded application but is not CPR certified. That user, Tony Oilo, has not yet responded. Although not shown, the entry could also be accompanied by a digital clock that shows the elapsed time since the responder has been invited so that, after a time, the dispatcher can cancel the invitation and invite a different candidate.

The confirmed responder's area 510 shows two responders who were invited and responded affirmatively, and thus are presumptively en route to the victim. These responders are again, a level 1 responder and a level 4 responder, who may be a general physician (where level 6 responders could be emergency room or critical care physicians). Dr. Langhans in this example is relatively close to the park where the victim is located, and thus may be expected to arrive there soon.

The various features here may be deployed in as supplements to, or integral portions of, existing emergency response systems and services, such as the RESCUENET line of products and services from ZOLL Medical Corporation, of Broomfield, Colo. For example, the screen shot 600 shown here may be generated by, or may augment a computer-aided dispatch (CAD) service such as RESCUENET DISPATCH, which is an EMS CAD solution designed to increase the efficiency of a dispatch center. The DISPATCH product helps to streamline call-taking and dispatch while reducing response times, using modules that collect trip information so that future calls can be more efficient. Also, RESCUENET WEB VIEWER can enable a dispatcher or other user to monitor the status of rescue vehicles, and the NETTRANSIT.COM service may allow customers to make online transport requests and inquiries, as well as to monitor call status.

The RESCUENET NAVIGATOR provides a mobile data computer (MDC) for use in rescue vehicles, and can be used to deliver information to, and receive information from, professional responders in the various manners discussed above. Separately from the processes discussed above, existing NAVIGATOR systems can provide a visual map (generated by RESCUENET COMMCAD) to a crew with turn-by-turn directions to a scene, can be used to measure on-time performance, collect incident timestamps, and integrate the obtained information into an incident report.

Other RESCUENET services and product can provide for crew scheduling, resource planning, review of code from resuscitators and defibrillators (Code Review), for reviewing overall performance of a dispatching system (Insight), to manage recordkeeping (FireRMS), and perform a variety of other functions.

Figure 6:
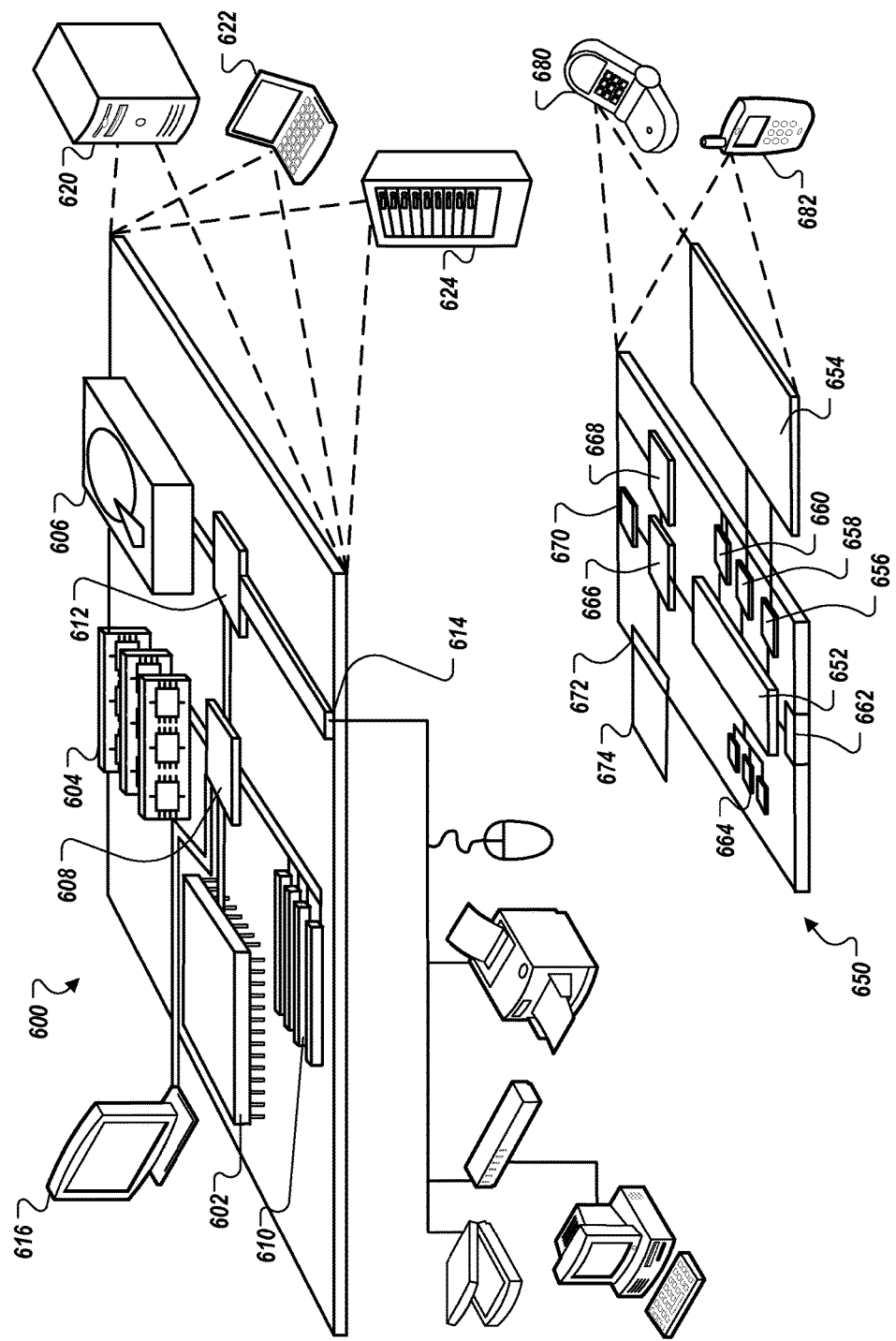
FIG. 6 shows an example of a generic computer device and a generic mobile computer device, which may be used with the techniques described here.

FIG. 6 shows an example of a generic computer device 600 and a generic mobile computer device 650, which may be used with the techniques described here. Computing device 600 is intended to represent various forms of digital computers, such as laptops, desktops, workstations, personal digital assistants, servers, blade servers, mainframes, and other appropriate computers. Computing device 650 is intended to represent various forms of mobile devices, such as personal digital assistants, cellular telephones, smartphones, and other similar computing devices. The components shown here, their connections and relationships, and their functions, are meant to be exemplary only, and are not meant to limit implementations of the inventions described and/or claimed in this document.

Computing device 600 includes a processor 602, memory 604, a storage device 606, a high-speed interface 608 connecting to memory 604 and high-speed expansion ports 610, and a low speed interface 612 connecting to low speed bus 614 and storage device 606. Each of the components 602, 604, 606, 608, 610, and 612, are interconnected using various busses, and may be mounted on a common motherboard or in other manners as appropriate. The processor 602 can process instructions for execution within the computing device 600, including instructions stored in the memory 604 or on the storage device 606 to display graphical information for a GUI on an external input/output device, such as display 616 coupled to high speed interface 608. In other implementations, multiple processors and/or multiple buses may be used, as appropriate, along with multiple memories and types of memory. Also, multiple computing devices 600 may be connected, with each device providing portions of the necessary operations (e.g., as a server bank, a group of blade servers, or a multi-processor system).

The memory 604 stores information within the computing device 600. In one implementation, the memory 604 is a volatile memory unit or units. In another implementation, the memory 604 is a non-volatile memory unit or units. The memory 604 may also be another form of computer-readable medium, such as a magnetic or optical disk.

The storage device 606 is capable of providing mass storage for the computing device 600. In one implementation, the storage device 606 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 604, the storage device 606, memory on processor 602, or a propagated signal.

The high speed controller 608 manages bandwidth-intensive operations for the computing device 600, while the low speed controller 612 manages lower bandwidth-intensive operations. Such allocation of functions is exemplary only. In one implementation, the high-speed controller 608 is coupled to memory 604, display 616 (e.g., through a graphics processor or accelerator), and to high-speed expansion ports 610, which may accept various expansion cards (not shown). In the implementation, low-speed controller 612 is coupled to storage device 606 and low-speed expansion port 614. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 600 may be implemented in a number of different forms, as shown in the figure. For example, it may be implemented as a standard server 620, or multiple times in a group of such servers. It may also be implemented as part of a rack server system 624. In addition, it may be implemented in a personal computer such as a laptop computer 622. Alternatively, components from computing device 600 may be combined with other components in a mobile device (not shown), such as device 650. Each of such devices may contain one or more of computing device 600, 650, and an entire system may be made up of multiple computing devices 600, 650 communicating with each other.

Computing device 650 includes a processor 652, memory 664, and an input/output device such as a display 654, a communication interface 666, and a transceiver 668, among other components. The device 650 may also be provided with a storage device, such as a microdrive or other device, to provide additional storage. Each of the components 650, 652, 664, 654, 666, and 668, are interconnected using various buses, and several of the components may be mounted on a common motherboard or in other manners as appropriate.

The processor 652 can execute instructions within the computing device 650, including instructions stored in the memory 664. The processor may be implemented as a chipset of chips that include separate and multiple analog and digital processors. The processor may provide, for example, for coordination of the other components of the device 650, such as control of user interfaces, applications run by device 650, and wireless communication by device 650.

Processor 652 may communicate with a user through control interface 658 and display interface 656 coupled to a display 654. The display 654 may be, for example, a TFT LCD (Thin-Film-Transistor Liquid Crystal Display) or an OLED (Organic Light Emitting Diode) display, or other appropriate display technology. The display interface 656 may comprise appropriate circuitry for driving the display 654 to present graphical and other information to a user. The control interface 658 may receive commands from a user and convert them for submission to the processor 652. In addition, an external interface 662 may be provide in communication with processor 652, so as to enable near area communication of device 650 with other devices. External interface 662 may provide, for example, for wired communication in some implementations, or for wireless communication in other implementations, and multiple interfaces may also be used.

The memory 664 stores information within the computing device 650. The memory 664 can be implemented as one or more of a computer-readable medium or media, a volatile memory unit or units, or a non-volatile memory unit or units. Expansion memory 674 may also be provided and connected to device 650 through expansion interface 672, which may include, for example, a SIMM (Single In Line Memory Module) card interface. Such expansion memory 674 may provide extra storage space for device 650, or may also store applications or other information for device 650. Specifically, expansion memory 674 may include instructions to carry out or supplement the processes described above, and may include secure information also. Thus, for example, expansion memory 674 may be provide as a security module for device 650, and may be programmed with instructions that permit secure use of device 650. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 664, expansion memory 674, memory on processor 652, or a propagated signal that may be received, for example, over transceiver 668 or external interface 662.

Device 650 may communicate wirelessly through communication interface 666, which may include digital signal processing circuitry where necessary. Communication interface 666 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 668. In addition, short-range communication may occur, such as using a Bluetooth, WiFi, or other such transceiver (not shown). In addition, GPS (Global Positioning System) receiver module 670 may provide additional navigation- and location-related wireless data to device 650, which may be used as appropriate by applications running on device 650.

Device 650 may also communicate audibly using audio codec 660, which may receive spoken information from a user and convert it to usable digital information. Audio codec 660 may likewise generate audible sound for a user, such as through a speaker, e.g., in a handset of device 650. Such sound may include sound from voice telephone calls, may include recorded sound (e.g., voice messages, music files, etc.) and may also include sound generated by applications operating on device 650.

The computing device 650 may be implemented in a number of different forms, as shown in the figure. For example, it may be implemented as a cellular telephone 680. It may also be implemented as part of a smartphone 682, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the invention. For example, much of this document has been described with respect to smartphones and similar client devices, but other forms of devices may be employed, including jackets for portable devices where the jackets have been provided with some or all of the functionality just described. For example, a jacket for a smart phone could be provided with a pair of metal plates in the jacket to form a large capacitor which may be used to measure force of a user pressing down on a victim's chest during CPR, and such sensed force may be passed to the smart phone, such as through a physical port on the smart phone or a wireless connection. patient monitoring and reporting may also be addressed.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

Figure 7:
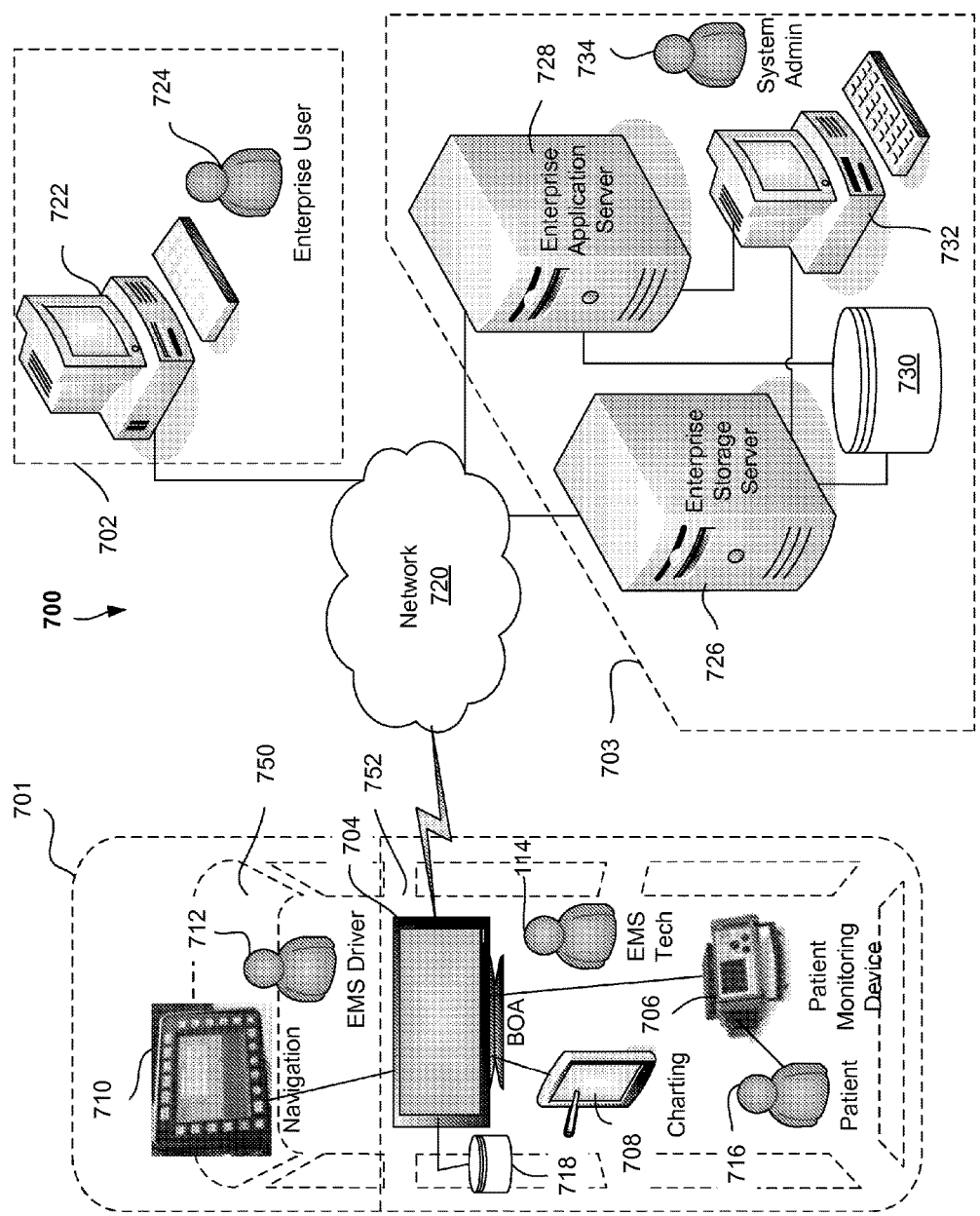
FIG. 7 shows a system that performs advanced data management, integration and presentation of EMS data from multiple different devices.

As illustrated in FIG. 7, a system 700 performs advanced data management, integration and presentation of EMS data from multiple different devices. In general, the system 700 includes a mobile environment 701, an enterprise environment 702, and an administration environment 703. Devices within the various environments 701, 702, 703 may be communicably coupled via a network 720, such as, for example, the Internet.

As used herein, the phrase "communicably coupled" is used in its broadest sense to refer to any coupling whereby information may be passed. Thus, for example, communicably coupled includes electrically coupled by, for example, a wire; optically coupled by, for example, an optical cable; and/or wirelessly coupled by, for example, a radio frequency or other transmission media. "Communicably coupled" also includes, for example, indirect coupling, such as through a network, or direct coupling.

The network 720 may also take the form of an ad hoc, self-configuring, self-healing network 2400 such as a MESH network. Wireless mesh networks 2400 are multihop systems in which devices assist each other in transmitting packets through the network, especially in adverse conditions. Such ad hoc networks may be implemented with minimal preparation, and they can provide a reliable, flexible system that can be extended to thousands of devices.

In a wireless mesh network, multiple nodes cooperate to relay a message to its destination. The mesh topology enhances the overall reliability of the network, which is particularly important when operating in harsh industrial environments. Like the Internet and other peer-to-peer router-based networks, a mesh network offers multiple redundant communications paths throughout the network. If one link fails for any reason (including the introduction of strong RF interference), the network automatically routes messages through alternate paths. In a mesh network, the distance between nodes can be shortened, which dramatically increases the link quality. Reducing the distance by a factor of two, the resulting signal is at least four times more powerful at the receiver. This makes links more reliable without increasing transmitter power in individual nodes. The reach of a mesh network may be extended, redundancy added, and general reliability improved simply by adding more notes.

A network may be a self-configuring and self-healing network. A network 2400 may not require a system administrator to tell it how to get a message to its destination. A mesh network can be self-organizing and does not require manual configuration. Because of this, adding new gear or relocating existing gear is as simple as plugging it in and turning it on. The network can discover the new node and automatically incorporates it into the existing system.

A mesh network is not only inherently reliable, it can also be highly adaptable. For example, if a tank-level sensor and data logger are placed too far apart for a robust RF communications link, one or more repeater nodes may be added to fill the gaps in the network.

On the Internet, if one router goes down, messages are sent through an alternate path by other routers. Similarly, if a device or its link in a mesh network fails, messages are sent around it via other devices. Loss of one or more nodes does not necessarily affect the network's operation. A mesh network is self-healing because human intervention is not necessary for re-routing of messages. Such networks provide redundancy and scalability.

In a mesh network, the degree of redundancy is essentially a function of node density. A network can be deliberately over-designed for reliability simply by adding extra nodes, so each device has two or more paths for sending data. This is a simpler way of obtaining redundancy than is possible in most other types of systems. A mesh network is also scalable and can handle hundreds or thousands of nodes. Because the operation of network 2400 does not depend on a central control point, adding multiple data collection points or gateways may be convenient.

Reliability, adaptability, and scalability are notable attributes of a wireless network for industrial control and sensing applications. Point-to-point networks provide reliability, but they are often challenging to scale to handle more than one pair of end points. Point-to-multipoint networks can handle more end points, but their reliability may depend on placement of the access point and end points. Mesh networks are inherently reliable, adapt easily to environmental or architectural constraints, and can scale to handle thousands of end points.

Referring again to FIG. 7, the mobile environment 701 is an ambulance or other EMS vehicle—for example a vehicular mobile environment (VME). The mobile environment may also be the local network of data entry devices as well as diagnostic and therapeutic devices established at time of treatment of a patient or patients in the field environment—the "At Scene Patient Mobile Environment" (ASPME). The mobile environment may also be a combination of one or more of VMEs and/or ASPMEs. The mobile environment may include a navigation device 710 used by the driver 712 to track the mobile environment's position 701, locate the mobile environment 701 and/or the emergency location, and locate the transport destination. The navigation device 710 may include a Global Positioning System ("GPS"), for example. The navigation device 710 may also be configured to perform calculations about vehicle speed, the travel time between locations, and estimated times of arrival. The navigation device 710 is located at the front of the ambulance to assist the driver 712 in navigating the vehicle. The navigation device 710 may be, for example, a RescueNet® Navigator onboard electronic data communication system available from Zoll Data Systems of Broomfield, Colo.

A patient monitoring device 706 and a patient charting device 708 are also often used for patient care in the mobile environment 701. The EMS technician 714 attaches the patient monitoring device 706 to the patient 716 to monitor the patient 716. The patient monitoring device 706 may be, for example, a defibrillator device with electrodes and/or sensors configured for attachment to the patient 716 to monitor heart rate and/or to generate electrocardiographs ("EGG's"). The patient monitoring device 106 may also include sensors to detect or a processor to derive or calculate other patient conditions. For example, the patient monitoring device 706 may monitor, detect, treat and/or derive or calculate blood pressure, temperature, respiration rate, blood oxygen level, end-tidal carbon dioxide level, pulmonary function, blood glucose level, and/or weight. The patient monitoring device 706 may be a loll E-Series defibrillator available from loll Medical Corporation of Chelmsford, Mass. A patient monitoring device may also be a patient treatment device, or another kind of device that includes patient monitoring and/or patient treatment capabilities.

The patient charting device 108 is a device used by the EMS technician 714 to generate records and/or notes about the patient's 716 condition and/or treatments applied to the patient. For example, the patient charting device 708 may be used to note a dosage of medicine given to the patient 716 at a particular time. The patient charting device 708 and/or patient monitoring device 706 may have a clock, which may be synchronized with an external time source such as a network or a satellite to prevent the EMS technician from having to manually enter a time of treatment or observation (or having to attempt to estimate the time of treatment for charting purposes long after the treatment was administered). The patient charting device 708 may also be used to record biographic and/or demographic and/or historical information about a patient, for example the patient's name, identification number, height, weight, and/or medical history. The patient charting device 108 can be a tablet PC, such as for example the TabletPCR component of the RescueNet ePCR Suite available from Zoll Data Systems of Broomfield, Colo. According to some embodiments, the patient charting device 108 is a wristband or smart-phone such as an Apple iPhone or iPad with interactive data entry interface such as a touch screen or voice recognition data entry that may be communicably connected to the BOA device 704 and tapped to indicate what was done with the patient 716 and when it was done.

The navigation device 710, the charting device 708, and the monitoring device 706 are each separately very useful to the EMS drivers 712 and technicians 714 before, during, and after the patient transport. A "back of ambulance" ("BOA") device 704 receives, organizes, stores, and displays data from each device 708, 710, 712 to further enhance the usefulness of each device 708, 710, 712 and to make it much easier for the EMS technician 714 to perform certain tasks that would normally require the EMS technician 714 to divert visual and manual attention to each device 708, 710, 712 separately. In other words, the BOA device centralizes and organizes information that would normally be de-centralized and disorganized.

Although device 704 is referred to herein as a "back of ambulance" device because the EMS technician 714 would normally benefit the most from having such a display device mounted in the back 752 of an ambulance, one of ordinary skill in the art, based on the disclosure provided herein, will recognize that some or all of the BOA device 704 may be located in any part of a mobile environment 701, EMS vehicle, and/or anywhere else useful to an EMS technician 714. For example, the BOA device 104 may be located in the front 750 of an ambulance, and/or may include components that are portable and can be carried into a patient residence.

The BOA device 704 is communicably coupled to the patient monitoring device 706, the patient charting device 708, and the navigation device 710. The BOA device 704 is also communicably coupled to a storage medium 718. The BOA device 704 may be a touch-screen, flat panel PC, and the storage medium 718 may be located within or external to the BOA device 704. The BOA device 704 may include a display template serving as a graphical user interface, which permits the user (e.g. EMS tech 714) to select different subsets and/or display modes of the information gathered from and/or sent to devices 706, 708, 710.

Figure 8:
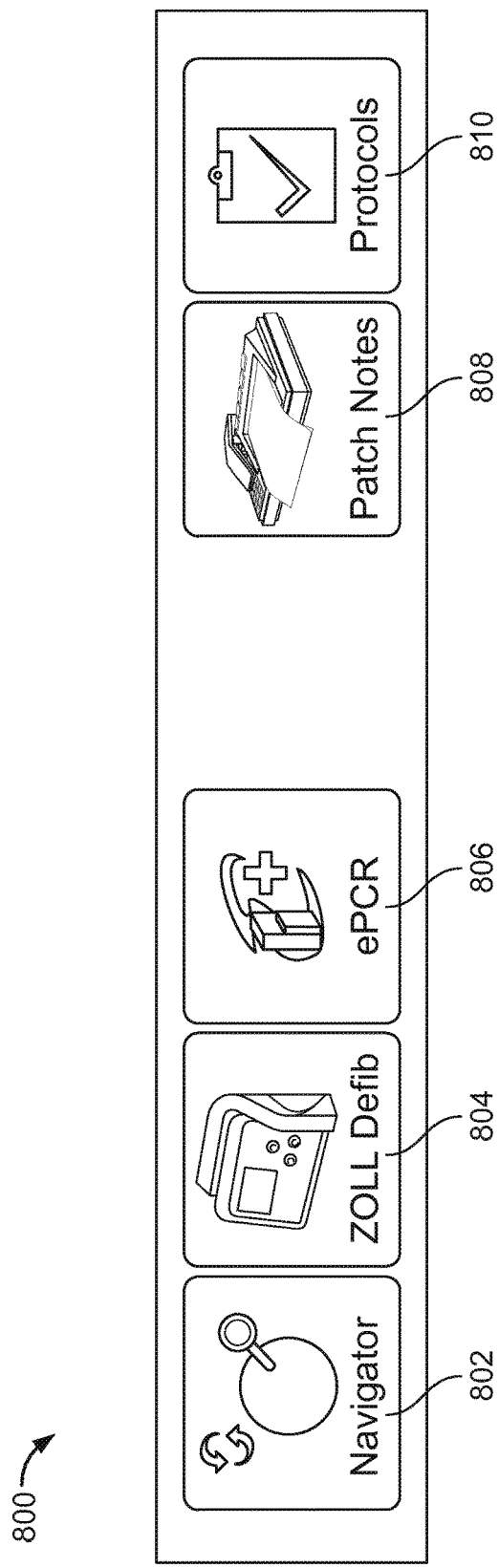
FIG. 8 illustrates one example of a menu template for a device display.

FIG. 8 illustrates one example of a menu template 800 for the display of BOA device 704. The menu template 800 includes a navigation button 802, a patient monitoring device button 804, a patient charting device button 806, a "patch notes" button 808, and a protocols button 810. Pressing one of the buttons takes the user (e.g. EMS tech 714) to a particular page displaying all or a subset of information from devices 706, 708, 710. Figures illustrate examples of particular information templates according to which information from the one or more EMS devices 706, 708, 710 is displayed.

Figure 9:
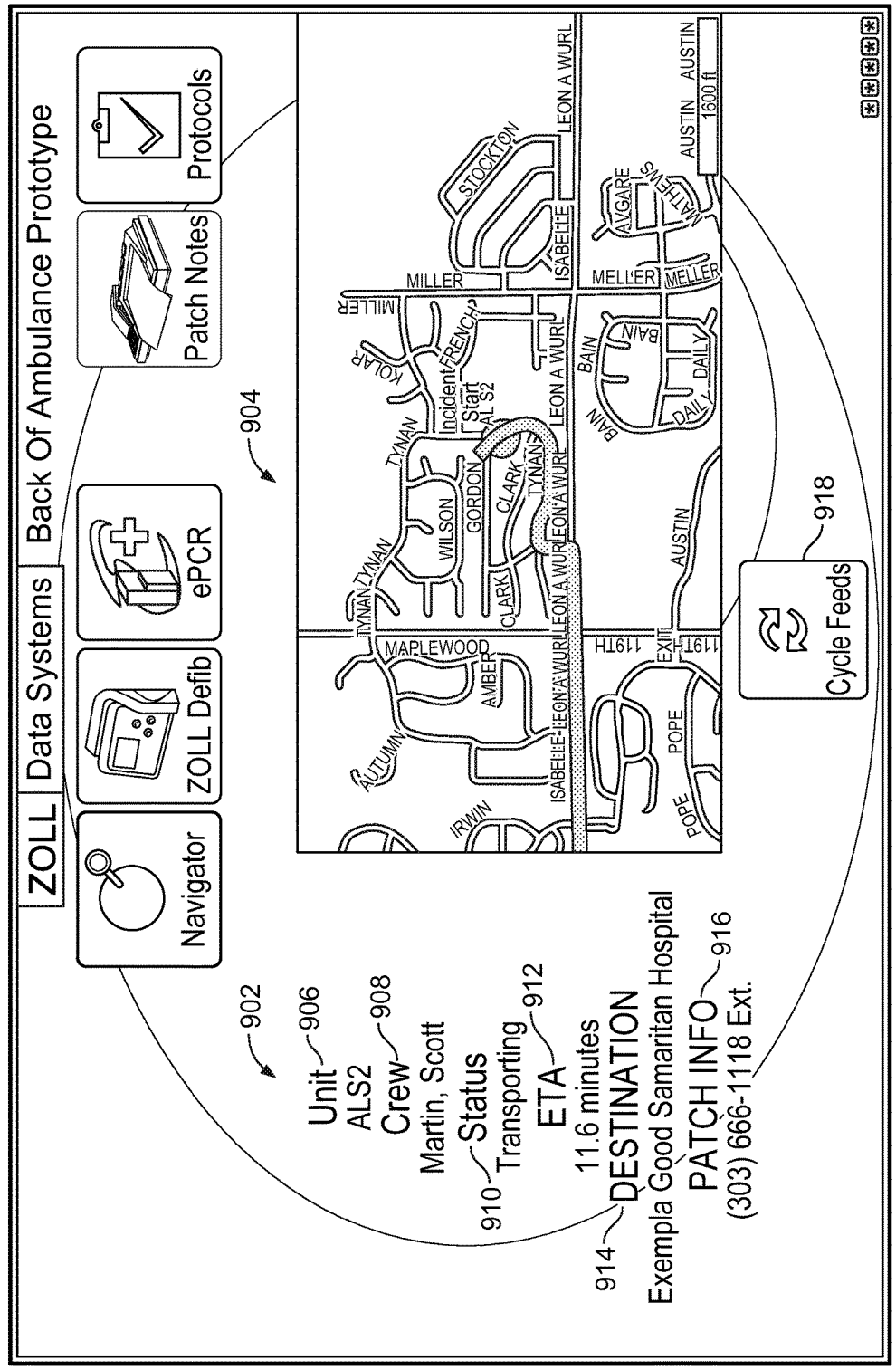
FIG. 9 illustrates a graphical user interface displayed when the user selects a navigation button on a device.

FIG. 9 illustrates a graphical user interface displayed when the user selects the navigation button 802. One part of the display includes a status section 902 and another part of the display includes a map section 904. The status section 902 includes one or more fields identifying information about the EMS vehicle trip. For example, the fields of the status section 902 may include one or more of a Unit field 906 identifying the name of the EMS vehicle for which information is displayed, a Crew unit 908 identifying one or more crew members of the EMS vehicle, a Status unit 910 identifying the status of the trip (e.g. "transporting" or "en route to patient"), an ETA field 912 identifying an estimated time of arrival at the destination, a Destination field 914 identifying the destination of the EMS vehicle (e.g. the hospital), and a Patch Info field 916 identifying a phone number or other information for contacting the EMS vehicle destination (e.g. the hospital).

The map section 904 may display street information along with the origin, destination, route identification, and/or progress information. The navigation device 710 may also supply vehicle status information for display, which may also be useful when a transport has not yet begun. A user may select a Cycle Feeds button 918 in order to continuously transition the display between one or more of the various displays. The information illustrated in FIG. 9 would normally be available only to the driver 712 in the front of the ambulance 701, but because BOA device 704 is communicably coupled to the navigation device 710, the BOA device 704 can display all or a selected subset of the information available to the navigation device 710.

Where community responders have identified themselves or have been identified by a dispatcher, the map section 904. The system shown in the above figures may also be able to provide additional functionality to a responder such as an EMT. For example, the BOA device 704, in communication with the navigation device 710, may be configured to provide additional mapping and/or navigation information. The BOA device 704 may display status information about a hospital destination, and may indicate diversion or alternative destinations to direct the ambulance 701 to an appropriate destination. The BOA device 704 may also display characteristics about hospitals and/or other destinations, such as the hospital's capabilities (e.g. heart specialty, burn specialty), insurance accepted, patient capacity and current patient capacity status. The BOA device 704 may also be in communication with the enterprise workstation 722 of the hospital or other destination to permit preregistration or partial preregistration of the patient 716. A hospital without availability shows up for the ambulance driver 712 as not available. The BOA device 704 may be configured to display such information simultaneously with a map and/or during navigation, to facilitate destination selection. This information may be obtained over the network 720 from an enterprise server 726 or 728 and/or from an enterprise workstation 722 and/or from the navigation device 710.

The BOA device 704 may also be configured to communicate in various ways with the user, including with the EMS driver 712 and/or the EMS technician 714. For example, the BOA device 704 may be configured to provide audio prompts, alarms, scheduling, timing, and/or audio streams to EMS users. The BOA device 704 may be configured with BLUETOOTH connectivity or capability, such that a user may connect or pair a unique BLUETOOTH device with BOA 704 to receive audio information and/or to communicate voice prompts. An alarm may be configured to sound or to display visually upon a triggering event, for example upon receipt by the BOA device 704 of an asynchronous event signal from a sensor indicating that a detected parameter is outside an acceptable range or value. Audio and/or visual cues may be used to alert a user to a particular dosage schedule, for example beeping when a certain amount of time has elapsed since a first administration of a drug. Such alarms and/or schedules may be set or customized by the users, or may be selected from a predetermined set of alarm and scheduling options.

The BOA device 704 may also provide role-based data and/or audio streams; for example, a technician administering CPR may receive audio and/or visual information about the patient's cardiac condition, but the BOA device 704 may filter out other information such as mapping and/or routing information for that user. Private, customized feedback and/or information may be provided to EMS users based on their roles.

The BOA device 704 may further provide decision support for an EMS technician. Based on information entered by the technician 714 (e.g. via a patient charting device 708) and/or information received from a patient monitoring device 106, BOA device 704 may compare the information with internal or external databases to display or otherwise convey a differential diagnosis, and/or predictive diagnosis (e.g. based on vectors or EKG information). For example, the BOA device 704 may present the EMS technician 714 with a decision matrix based on symptoms and/or responses to treatments to help the EMS technician 714 determine, for example in an interactive format, a potential diagnosis. The BOA device 704 may provide protocols or links to protocols based on the information received, either from the technician 714 or from one of the devices with which it is in communication.

In one embodiment, the data for the patient's history may be entered via the BOA device 704 with patient physiological measures via the monitor of BOA device 704. As the differential diagnosis requires both patient history, patient examination findings, and measures of the patient's physiological state via such monitoring as ECG, capnography and pulse oximetry, these data elements are integrated into a user interface that automatically or semi-automatically integrates the various data elements on a single differential diagnosis screen within the application on the BOA device 704. The interface of BOA 704 begins by asking the rescuer to choose from a list of common presenting symptoms or complaints by the patient, e.g. dyspnea or respiratory distress. As patient history and physical examination findings are entered into the BOA device 704, the differential diagnosis page may gradually narrow down the possible diagnoses. Heart sound measurement and detection may be incorporated into the monitoring device 706 for the detection of S3 and S4 heart sounds and automatically narrow the differential, or suggest for the rescuer to confirm agreement with the software diagnosis, of heart failure or pulmonary edema. Pulse oximetry and capnography are also very helpful measures and may be automatically incorporated into the algorithm for more accurate diagnosis.

In one embodiment, rescuers may be able to simply touch the cursor to the history or physical exam findings listed as possible, thereby minimizing unnecessary keying inputs. At the bottom of each list of possible findings or history can be a data entry position for "Other", for those findings or history which are not normally consistent with the presenting condition. In one embodiment, these additional findings, history or physiological measurements can be compared with a larger differential diagnosis database to suggest other possibilities to the rescuer based on a calculated probability or if the other possible causes have been ruled out.

In much the same way that twelve-lead data and other BOA 704 device data may be sent to an enterprise environment 702 and displayed and/or retrieved on an enterprise workstation 722 or web-based environment, the BOA device 704 may also be configured to receive, display, and/or store similar information from an enterprise environment 702. For example, in a situation in which a patient is being transported from one hospital to another to receive specialized care, the hospital may send to the BOA device 704 information about the patient's vitals and/or health history and/or physician recommendations. Alternatively, the hospital may grant electronic authorization for the remote EMS technician to query its database or databases where such information is kept, to enable the EMS technician 714 to select, using the BOA device 704 interface, which and how much information he would like to receive. In this way, technicians in an ambulance 701 can see what is happening to a patient at the hospital, for example.

The BOA device 704 may also include speech recognition software and/or text-to-speech software. As such, the BOA device 704 may provide an audio signal that reads text or numeric data received from one or more devices, to convey the data to the EMS technician 714 audibly, such that the EMS technician 714 need not divert visual attention from the patient or from another task. The BOA device 704 may also recognize voice command prompts, to enable the user to operate the BOA device 704 by voice instead of having to divert manual attention from the patient or the task at hand.

The BOA device 704 also be configured to retrieve audio data stored on a device, such as a patient monitoring device 706, to help the EMS technician 714 in treatment or diagnosis, and/or for storage, technician evaluation, quality control, or later playback. For example, the patient monitoring device 714 may be a defibrillator that records a continuous audio stream; the BOA device 704 may access the continuous audio stream and permit selective play back of certain portions and/or transmit the audio stream or audio file for remote access or storage. The BOA device 704 may also be configured to receive audio information from a patient monitoring device 706 or other device even before the EMS technician 714 has reached the patient, to help the EMS technician 714 to prepare for the scene.

The BOA device 704 may be configured to connect with a video monitoring device, for example a webcam, or a standalone video camera, and/or a video capture device that is mounted on or part of another device to which the BOA device 704 connects. For example, a video or still camera mounted in the back of an ambulance 701 may provide visual data to BOA 704 for storage and/or transmission and/or retransmission to the enterprise environment 702 and/or the administration environment 703. Such a video feed may permit a physician waiting at a hospital to view the patient's status before the patient arrives, for example.

With an ability to connect with and interface multiple EMS-related devices, both clinical and non-clinical, and aggregate such EMS-information (both clinical and non-clinical) from multiple devices, the BOA device 704 may also be configured for inventory monitoring and control. For example, the BOA device 704 may be communicably coupled with a bar code scanner, a radio frequency identification ("RFIO") receiver or transceiver, or other inventory monitoring device. The BOA device 704 may maintain or communicate with a database that tracks a particular set of inventoried items, whether they be medical devices, supplies, drugs, personnel, or the like.

For example, the BOA device 704 may include a database that tracks the inventory of devices, supplies, and drugs on board a particular ambulance 701. When a new device is placed on the ambulance 701, the new device is equipped with a tag or bar code or some other unique identifier, and the BOA device 704 may be configured to automatically sense, or to be instructed to sense (e.g. by scanning a bar code with the bar code scanner), the presence of a new inventory item. The BOA device 704 may also prompt the user with a status update request, for example: new item, item being removed, item being dispensed, item destroyed, item transferred. Hence, at the beginning of an ambulance 701 shift, the crew may query the BOA device 704 to display the inventory of devices, supplies, and/or drugs on board, and may supplement the inventory for any deficient item. When a drug is administered, it may be scanned into the BOA device 704 system with an indication that it has been dispensed and should be replaced. At the end of a shift, the crew may check the inventory via the BOA device 704 and restock necessary supplies and/or transmit the inventory situation to a third party for any appropriate restocking, monitoring, and/or verification activity.

Such inventory information may also be conveyed by BOA 704 for remote use and/or storage. For example, a defibrillator patient monitoring device 106 may be checked out to each crew of each ambulance 701, and this information may be sent by BOA device 704 through network 720 to the enterprise storage server 726, which may aggregate such information across multiple ambulances 701. A shift supervisor using a remote enterprise workstation 722 may query such database to determine which defibrillators are out in the field on which ambulances 701. In this way, the BOA device 704 may auto-upload inventory information to a central system.

The BOA device 704 may also be configured to connect with devices (clinical and/or non-clinical) that track EMS technician 714 and patient 716 safety. For example, the BOA device 704 may be configured to connect with accelerometer and/or tire pressure sensors, and/or other vehicle-relate sensors to track driving conditions, driving behavior, safety level, and/or event occurrences. According to one embodiment, the BOA device 704 may be configured to connect with a breathalyzer device, which may be used to sense and/or estimate the blood alcohol content of the driver and/or patient. The BOA device 704 may collect such data and display it to the user in a feedback format, and/or may send such data through the network 720 for storage and/or remote evaluation. The BOA device 104 may also monitor a vehicle's maintenance schedule and alert the user when maintenance is needed or recommended.

Due to its connection with the network 720 and also with other devices 706, 108, 710, the BOA device 704 may also serve as an ambulance headquarters and/or a type of "repeater" in a trauma or disaster situation. For example, the BOA device 704 may be configured to connect with multiple devices including devices outside the ambulance 701 and/or in a different ambulance 701, to permit the BOA device 704 user to view and manage response treatments, for example. Such a configuration also permits data from multiple devices (e.g. multiple defibrillators or other patient monitoring devices) to be conveyed through the network 720 to an enterprise environment 702 and/or administration environment 703. In another example, a single ambulance 701 equipped with a BOA device 704 system as described above may be deployed to a disaster or trauma situation, and the BOA device 704 may be connected to and aggregating information from multiple patient monitoring devices 706. A supervisor or situation manager may use the BOA device 704 to monitor treatment status, prioritize patient medical needs, transmit relevant information to selected outside caregivers, hospitals, and/or treatment centers, and to distribute resources accordingly.

According to some embodiments, the BOA device 704 is configured to perform diagnostics on and/or to initiate self-diagnostics for devices with which it is connected. The BOA device 704 may also be used for training and/or education of EMS technicians 714, by making downloaded protocols available for display, and/or by simulating a medical emergency (e.g. simulating the device feeds from multiple clinical and non-clinical devices during a medical emergency or transport).

According to some embodiments, the BOA device 704 provides a visual indication of whether its connection with the navigation device 710 (or other predetermined device) is online or offline. The user can select to view historical rather than current patient information; for example, the user may select to view thumbnails of previous twelveleads, and can send a collection of twelve-lead data snapshots to an enterprise environment 702 (e.g. a hospital), each with a unique serial number, for example. The enterprise user 724 may also view the patch notes from the BOA device 704, so that the EMS technician 714 need not convey them telephonically.

The BOA device 704 may also include a drop-down menu interface, listing each device to which the BOA device 704 is connected and its connection status. The BOA device 704 may also be connected with a biometric device such as a fingerprint reader or a retinal scanner, or a non-biometric device such as a keypad, to assist in verifying the identity of a patient and/or in authorizing access to patient medical records. Such records may be stored in remote databases and/or stored by different entities, for example.

Figure 10:
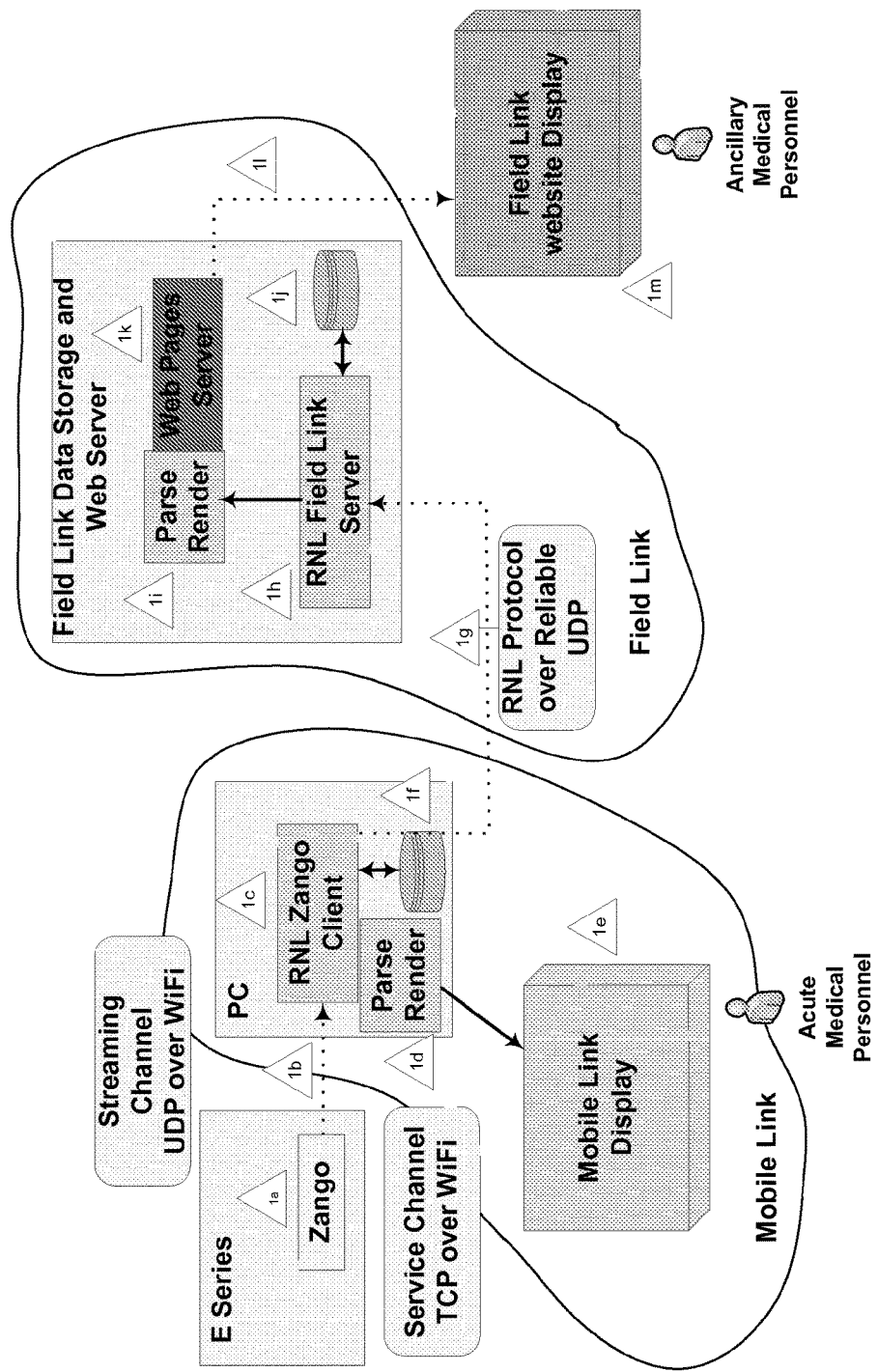
FIG. 10 illustrates a data transmission interface.

FIG. 10 illustrates a data transmission interface. Zango device (1 *a*), can be configured to perform a number of functions, such as:

Frame defibrillator incident data blocks.
Stream framed incident data.
Save incident data frames to Zango database.
Host a set of data management services upon the Zango database.
  In one embodiment, data management services are read/erase only. Services to modify incident data are not supplied.

The "EMS communications interface channel" (1 *a*, 1 *b*, 1 *c*) provides a mechanism to transmit patient monitoring data (e.g. E Series data) to the BOA device 704. This channel uses the device 2000 to connect to BOA 104.

The RNI Zango Client (1 *c*) can be configured to perform a number of functions, such as:

Receive streamed incident frame data (1 *b*).
Present incident frame data on the Mobile Link Display (1 *e*) (parse, render, 1 *d*).
Store incident frame data into the Mobile Link database (1*f*)
Host a set of data management services upon the Mobile Link database (1*f*).
  In some embodiments, data management services are read/erase only; and services to modify incident data are not supplied.
Forward 12 lead ecg and vitals data to Field Link. (1 *g*)
Consume Zango data management services (1 *b*).

The following table lists and describes various elements of FIG. 10, described with respect to one embodiment.

| Notation (FIG. 10) | Description | Notes |
| --- | --- | --- |
| 1a | Zango accessory | Data management for accessory for ZOLL E Series. Captures, stores, and transmits E Series data written to the E Series data slot to connect the E Series data to RNL. |
| 1b | Zango UDP/IP transmissions over WPA2 secured 802.11 | |
| 1b | Zango TCP/IP service invocation response transactions over WPA2 secured 802.11 | |
| 1c | RNL Zango Client | RNL receiver of Zango Transmissions. |
| 1a, 1b, 1c | Zango channel | |
| 1d | Zango parsing and rendering engine | Zango messages fromt h E Series are parsed and rendered for acute medical viewing. |
| 1e | Mobile Link Display | |
| 1f | Mobile Link Storage | |
| 1g | RNL Protocol: Reliable UDP/IP over secured cellular networks. | |
| 1h | RNL Field Link Server | Mobile link message receiver in Field Link environment. |
| 1c, 1g, 1h | RNL Mobile Link to Field Link Communications | The RNL mobile Link to Field Link Channel connects Mobile Link to |
| 1j | Channel | Field Link using reliable UDP/IP over secured cellular networks. |
| 1j | Field Link Storage | |
| 1i | Field Link parsing and rendering engine | |
| 1k | Field Link web server | |
| 1l | Secured connection to Field Link users | |
| 1m | Field Link web viewer | |

Figure 11:
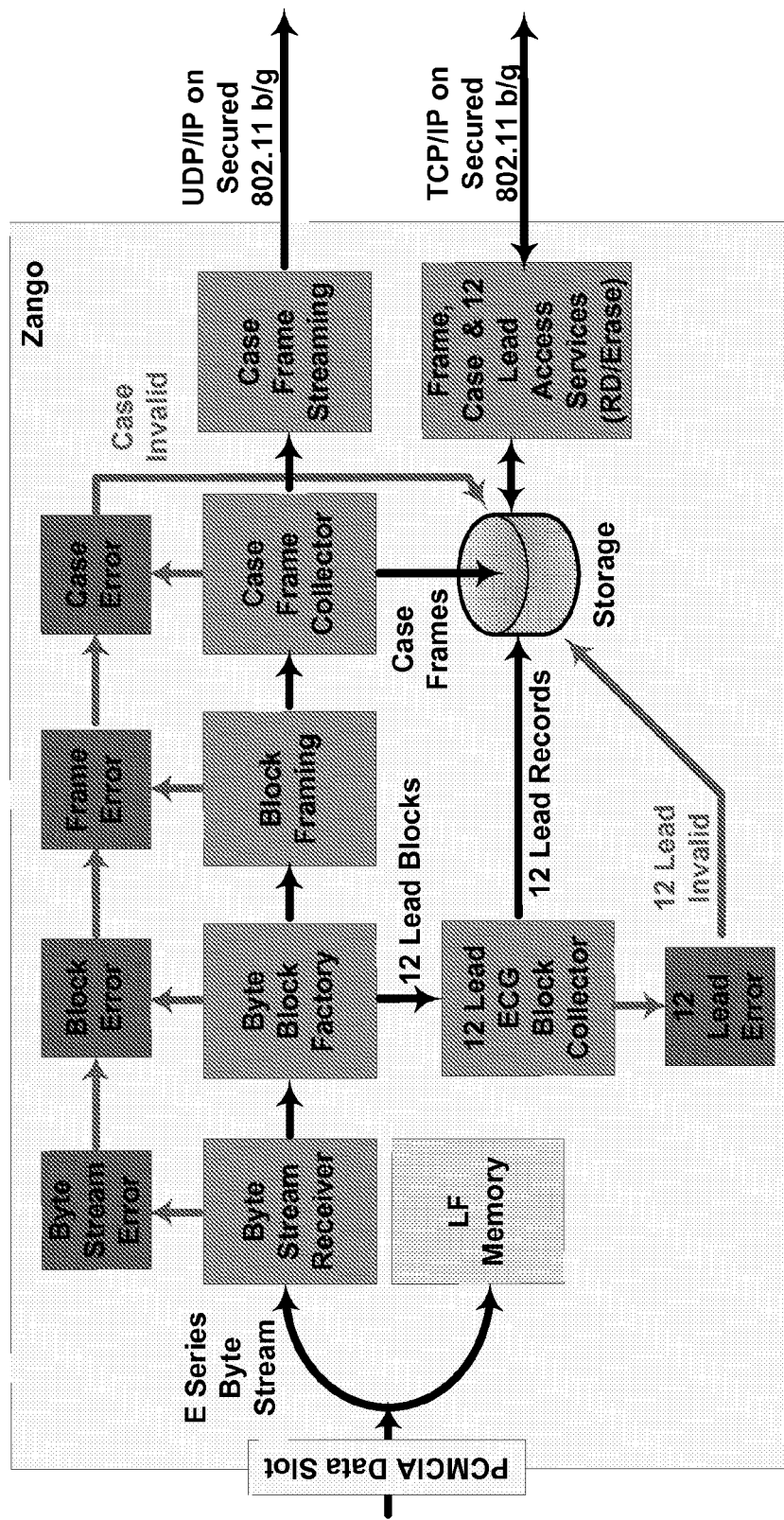
FIG. 11 illustrates an EMS communication interface transmission processing block diagram

FIG. 11 illustrates an EMS communication interface transmission processing block diagram. The E Series writes a continuous byte stream of data to the PCMCIA Data Slot. The byte stream consists of E Series data block messages some of which are sent periodically and some of which are sent episodically. An example a periodic message is the ecg message. The E Series writes the ecg values for the currently displayed lead once per 100 ms, the message contains 25 data values (250 Hz samples, 4 ms apart).

Examples of episodic messages are the vital sign messages. The E Series sends a particular vital sign message when a particular vital sign parameter value has changed; asynchronous messages are sent with no particular frequency.

The byte stream is bifurcated at the input to the Zango card. One branch stores data into an on board (16 MB) linear flash, replicating all of the E Series linear flash operations. All data written is stored in the linear flash subsystem. The interface is hardware level, instant on prepared to receive and save the E Series byte stream to flash subsystem.

The second byte stream branch goes into the processor side of the Zango card. The processor side of the Zango card functions to process the byte stream performing the logical operations illustrated in FIG. 11. In the non-faulted case the byte stream receiver passes bytes to the byte block factory. The byte block factory reconstructs E Series data block messages from the byte stream. In this operation, 12 lead ecg data blocks are reconstructed and managed on a separate path to the incident path (sets of 12 lead data blocks are collected into entire 12 lead messages). The 12 lead data is entirely preserved in the case stream. One of the reasons for storing them separately is to permit a service user to request to see a 12 lead record on the service channel, rather than uploading the entire incident to get the 12 lead data.

Blocks are then framed into a configurable time interval's worth of data blocks. For example, frames of one second in size might have on the order of 15 data blocks in the one second frame. Frames are collected into constructs of cases or incidents. Frames are stored in the Zango database. Complete incidents are marked (collection of all incident frames) and managed as incidents as they are completed. Frames are also streamed on WiFi where they can be received by authorized client applications, such as the RNL Zango Client.

The upper row of boxes in FIG. 11 identify detection and error handling processes for risk control of compromised data faults. Byte stream, block, framing, 12 Lead, or incident error all result in the following behaviors:

Data is marked as invalid.
Invalid data is not rendered for a user to view during the acute treatment phase of an incident
Data is stored marked as invalid for forensic analysis.

Anyone of these faults will cause the incident to be marked invalid.

Acute medical personnel are informed of data faults, assuming connectivity to RNL.

These are the control measures and behaviors that trace directly to the hazard analysis for data compromised faults.

Figure 12:
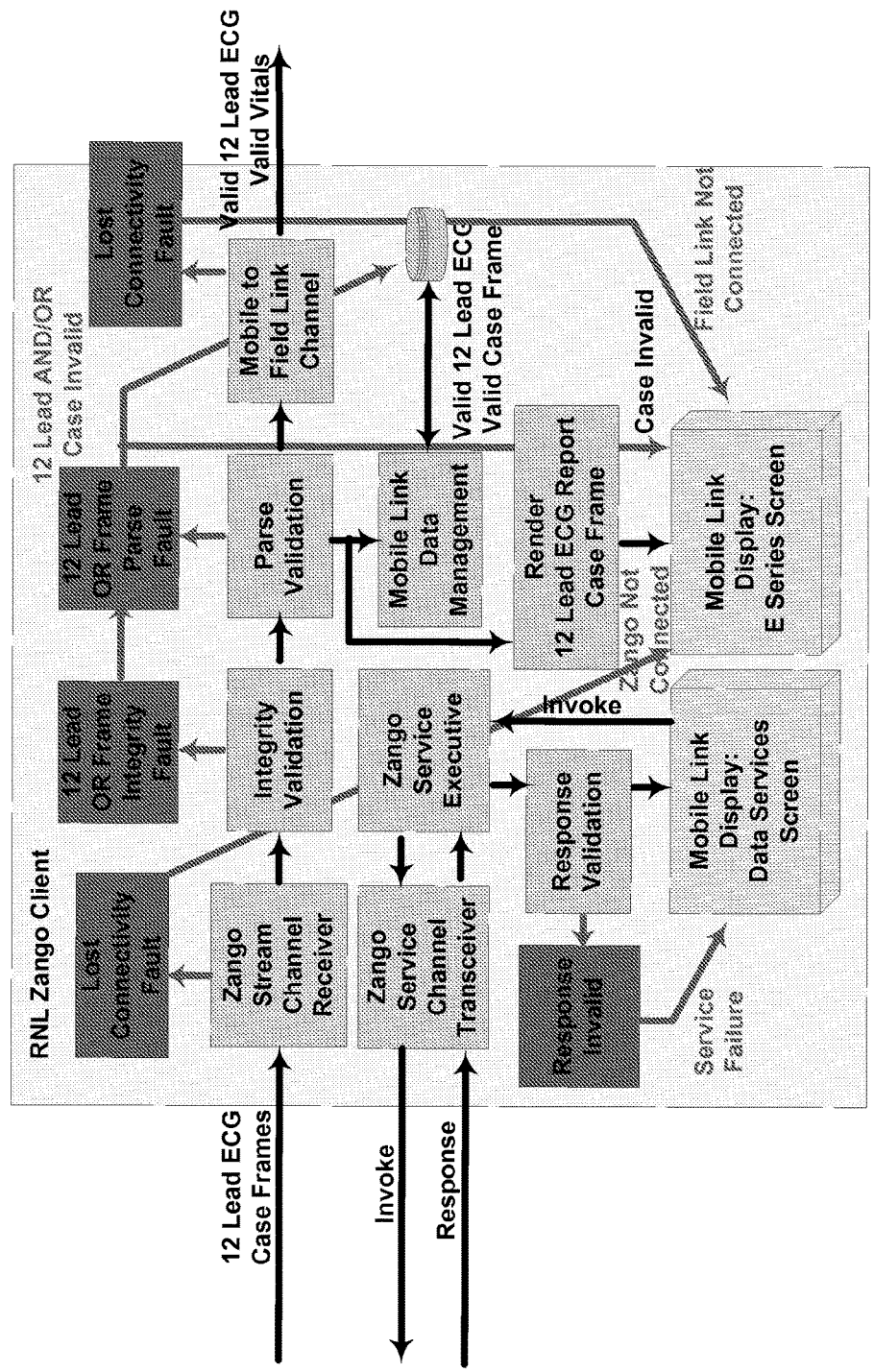
FIG. 12 illustrates a EMS communications interface device client architecture Like reference symbols in the various drawings indicate like elements.

FIG. 12 illustrates a EMS communications interface device client architecture. In some cases, Zango connectivity to RNL may be volatile as a result of the nature of wireless communications in mobile environments. For example, an E Series equipped with a Zango card may be moved out of range of the wireless access point to which it had been connected. When the device is back in range and reconnects, processing resumes as illustrated. Data written by the E Series while not connected to RNL is persisted in the Zango database and can be obtained in RNL upon re-connect.

The upper row of boxes in FIG. 12 identify detection and error handling processes for risk control of compromised data faults and communications faults. Integrity or framing faults detected on the streamed data result in the following behaviors:

Data is marked as invalid.

Invalid data is not rendered for a user to view during the acute treatment phase of an incident Data is stored marked as invalid for forensic analysis.

Either of these faults will cause the incident to marked invalid.

Acute medical personnel are informed of data faults for either 12 leads or case frames.

Acute medical personnel are informed of communications faults.

Acute medical personnel are informed of service faults.

Service responses are validated and invalid service responses are notified to the user and invalid data is not displayed. Connectivity status between Zango and the Zango Stream Channel Receiver is monitored and reported to users on the Mobile Link Display. Lost connectivity between Zango and RNL does not result in lost data as Zango stores data in the Zango database regardless of connection status. Service channel connectivity is not continuously monitored, service requests will fail (response invalid) if service connectivity is not present.

What is claimed is:

1. A medical equipment management system comprising a notification service comprising processor-executable instructions that are configured to cause a lay response server that is separate from a dispatch server to:
    post a sign-up software application that is Internet accessible;
    receive, prior to an emergency event and from the sign-up software application downloaded onto a mobile computing device associated with a lay responder, enrollment information provided to the sign-up software application by the lay responder and comprising lay responder information;
    associate the lay responder with an account for sending information to the mobile computing device associated with the lay responder;
    receive, from the dispatch server, emergency event information received by the dispatch server, wherein the emergency event information comprises a location of the emergency event;
    receive, from the mobile computing device associated with the lay responder, a location of the mobile computing device associated with the lay responder;
    receive storage location information for one or more publicly accessible automated external defibrillators (AEDs) via a volunteer survey of a geographic area comprising the one or more publicly accessible automated external defibrillators (AEDs); and
    based at least in part on the location of the emergency event, provide to the mobile computing device associated with the lay responder a notification about the emergency event that includes mapping information indicative of the location of the emergency event, the storage location information for the one or more publicly accessible AEDs, and the location of the mobile computing device associated with the lay responder relative to the location of the emergency event,
    wherein the one or more publicly accessible AEDs are in geographic proximity to the emergency event and
    wherein the storage location information is verified based on the volunteer survey of the geographic area.

2. The system of claim 1, wherein the storage location information comprises an availability of the one or more publicly accessible AEDs and the mapping information comprises the availability of the one or more publicly accessible AEDs.

3. The system of claim 1, wherein the processor-executable instructions are configured to cause the lay response server to receive, from the mobile computing device associated with the lay responder, an indication that the lay responder is available in response to the notification about the emergency event.

4. The system of claim 1, wherein the lay responder information comprises CPR training information.

5. The system of claim 1, wherein the lay responder is an individual that is not assigned responsibility by a lifesaving organization to serve emergency events.

6. The system of claim 1 wherein the processor-executable instructions are configured to cause the lay response server that is separate from the dispatch server to receive, via the sign-up software application, status information for the one or more publicly accessible AEDs.

7. The system of claim 6 wherein the status information for the one or more publicly accessible AEDs comprises one or more of an indication that the one or more publicly accessible AEDs are operational and an indication that the storage location information for the one or more publicly accessible AEDs is unchanged.

8. The system of claim 1 wherein the notification service is configured to provide the notification about the emergency event to the mobile computing device associated with the lay responder and is not configured to provide for dispatch of professional responders, wherein the professional responders are agents of an organization responsible for providing emergency services and the lay responder is not an agent of the organization responsible for providing emergency services.

9. The system of claim 1 wherein the dispatch server is configured to receive the emergency event information from a 911 calling network and to provide for dispatch of professional responders, wherein the professional responders are agents of an organization responsible for providing emergency services.

10. The system of claim 1 wherein the sign-up software application comprises a mapping application.

11. The system of claim 1 wherein the processor-executable instructions are configured to cause the lay response service to receive wireless communications from the one or more publicly accessible AEDs.

12. The system of claim 11 wherein the wireless communications from the one or more publicly accessible AEDs are indicative of a status of the one or more publicly accessible AEDs and wherein the processor-executable instructions are configured to cause the lay response server to monitor the status of the one or more publicly accessible AEDs.

13. A computer-implemented method for communicating information to medical responders, the method comprising:
posting a sign-up software application that is Internet accessible;
receiving, at a notification service of a lay response server that is separate from a dispatch server, prior to an emergency event and from the sign-up software application downloaded onto a mobile computing device associated with a lay responder, enrollment information provided to the sign-up software application by the lay responder and comprising lay responder information;
associating the lay responder with an account for sending information to the mobile computing device associated with the lay responder;
receiving, at the notification service of the lay response server, from the dispatch server, emergency event information received by the dispatch server, wherein the emergency event information comprises a location of the emergency event;
receiving, at the notification service of the lay response server, a location of the mobile computing device associated with the lay responder;
receiving storage location information for one or more publicly accessible automated external defibrillators (AEDs) based on a volunteer survey of a geographic area comprising the one or more publicly accessible automated external defibrillators (AEDs);
based at least in part on the location of the emergency event, providing, by the notification service of the lay response server, to the mobile computing device associated with the lay responder, a notification about the emergency event that includes mapping information indicative of the location of the emergency event, the storage location information for the one or more publicly accessible AEDs, and the location of the mobile computing device associated with the lay responder relative to the location of the emergency event,
wherein the one or more publicly accessible AEDs are in geographic proximity to the emergency event and
wherein the storage location information is verified based on the volunteer survey of the geographic area.

14. The method of claim 13 comprising receiving, at the lay response server via the sign-up software application, status information for the one or more publicly accessible AEDs.

15. The method of claim 14 wherein the status information for the one or more publicly accessible AEDs comprises one or more of an indication that the one or more publicly accessible AEDs are operational and an indication that the storage location information for the one or more publicly accessible AEDs is unchanged.

16. The method of claim 13 wherein the storage location information comprises an availability of the one or more publicly accessible AEDs and the mapping information comprises the availability of the one or more publicly accessible AEDs.

17. The method of claim 13 comprising receiving, at the lay response server from the mobile computing device associated with the lay responder, an indication that the lay responder is available in response to the notification about the emergency event.

18. The method of claim 13, wherein the lay responder information comprises CPR training information.

19. The method of claim 13, wherein the lay responder is an individual that is not assigned responsibility by a lifesaving organization to serve emergency events.

20. The method of claim 1 wherein the notification service is configured to provide the notification about the emergency event to the mobile computing device associated with the lay responder and is not configured to provide for dispatch of professional responders, wherein the professional responders are agents of an organization responsible for providing emergency services and the lay responder is not an agent of the organization responsible for providing emergency services.

21. The method of claim 1 wherein the dispatch server is configured to receive the emergency event information from a 911 calling network and to provide for dispatch of professional responders, wherein the professional responders are agents of an organization responsible for providing emergency services.

22. The method of claim 13 wherein the sign-up software application comprises a mapping application.

23. The method of claim 1 comprising receiving, at the lay response server, wireless communications from the one or more publicly accessible AEDs.

24. The method of claim 23 wherein the wireless communications from the one or more publicly accessible AEDs are indicative of a status of the one or more publicly accessible AEDs and comprising monitoring, by the lay response server, the status of the one or more publicly accessible AEDs.

25. A computer program product comprising computer-readable instructions tangibly embodied in a non-transitory computer-readable storage device, the instructions executable by one or more processing devices to cause a lay response server that is separate from a dispatch server to:
post a sign-up software application that is Internet accessible;
receive, at the lay response server that is separate from the dispatch server, prior to an emergency event and from the sign-up software application downloaded onto a mobile computing device associated with a lay responder, enrollment information provided to the sign-up software application by the lay responder and comprising lay responder information;
associate the lay responder with an account for sending information to the mobile computing device associated with the lay responder;
receive, at the lay response server, from the dispatch server, emergency event information received by the dispatch server, wherein the emergency event information comprises a location of the emergency event;
receive, from the mobile computing device associated with the lay responder, a location of the mobile computing device associated with the lay responder;
receive storage location information for one or more publicly accessible automated external defibrillators (AEDs) based on a volunteer survey of a geographic area comprising the one or more publicly accessible automated external defibrillators (AEDs);
based at least in part on the location of the emergency event, provide, by a notification service of the lay response server to the mobile computing device associated with the lay responder, a notification about the emergency event that includes mapping information indicative of the location of the emergency event, the storage location information for the one or more publicly accessible AEDs, and the location of the mobile computing device associated with the lay responder relative to the location of the emergency event,
wherein the one or more publicly accessible AEDs are in geographic proximity to the emergency event and
wherein the storage location information is verified based on the volunteer survey of the geographic area.

26. The computer program product of claim 25 wherein the instructions are executable by the one or more processing devices to cause the lay response server that is separate from the dispatch server to receive, via the sign-up software application, status information for the one or more publicly accessible AEDs.

27. The computer program product of claim 26 wherein the status information for the one or more publicly accessible AEDs comprises one or more of an indication that the one or more publicly accessible AEDs are operational and an indication that the storage location information for the one or more publicly accessible AEDs is unchanged.

28. The computer program product of claim 25 wherein the storage location information comprises an availability of the one or more publicly accessible AEDs and the mapping information comprises the availability of the one or more publicly accessible AEDs.

29. The computer program product of claim 25 wherein the instructions are executable by the one or more processing devices to cause the lay response server that is separate from the dispatch server to receive, from the mobile computing device associated with the lay responder, an indication that the lay responder is available in response to the notification about the emergency event.

30. The computer program product of claim 25, wherein the lay responder information comprises CPR training information.

31. The computer program product of claim 25, wherein the lay responder is an individual that is not assigned responsibility by a lifesaving organization to serve emergency events.

32. The computer program product of claim 25 wherein the notification service is configured to provide the notification about the emergency event to the mobile computing device associated with the lay responder and is not configured to provide for dispatch of professional responders, wherein the professional responders are agents of an organization responsible for providing emergency services and the lay responder is not an agent of the organization responsible for providing emergency services.

33. The computer program product of claim 25 wherein the dispatch server is configured to receive the emergency event information from a 911 calling network and to provide for dispatch of professional responders, wherein the professional responders are agents of an organization responsible for providing emergency services.

34. The computer program product of claim 25 wherein the sign-up software application comprises a mapping application.

35. The computer program product of claim 25 wherein the instructions are executable by the one or more processing devices to cause the lay response server that is separate from the dispatch server to receive wireless communications from the one or more publicly accessible AEDs.

36. The computer program product of claim 35 wherein the wireless communications from the one or more publicly accessible AEDs are indicative of a status of the one or more publicly accessible AEDs and wherein the instructions are executable by the one or more processing devices to cause the lay response server that is separate from the dispatch server to monitor the status of the one or more publicly accessible AEDs.

* * * * *

UNITED STATES PATENT AND TRADEMARK OFFICE
CERTIFICATE OF CORRECTION

PATENT NO. : 10,178,534 B2
APPLICATION NO. : 14/927851
DATED : January 8, 2019
INVENTOR(S) : David Barash et al.

Page 1 of 1

It is certified that error appears in the above-identified patent and that said Letters Patent is hereby corrected as shown below:

In the Specification

Column 6, Line 67, after "diagram", insert --.--
Column 7, Line 2, after "architecture", insert --.--
Column 33, Line 34, delete "patient", insert --Patient--
Column 40, Line 57, delete "twelveleads", insert --twelve leads--
Column 41, Line 55, delete "fromt h", insert --from the--
Column 43, Line 24, after "incident", insert --.--

In the Claims

Claim 20, Column 46, Line 4, delete "claim 1", insert --claim 13--
Claim 21, Column 46, Line 14, delete "claim 1", insert --claim 13--
Claim 23, Column 46, Line 22, delete "claim 1", insert --claim 13--

Signed and Sealed this
Ninth Day of April, 2019

Andrei Iancu
*Director of the United States Patent and Trademark Office*